(12) United States Patent
Peyman

(10) Patent No.: US 9,233,157 B2
(45) Date of Patent: Jan. 12, 2016

(54) METHOD AND COMPOSITION FOR HYPERTHERMALLY TREATING CELLS

(71) Applicant: Gholam A. Peyman, Sun City, AZ (US)

(72) Inventor: Gholam A. Peyman, Sun City, AZ (US)

(*) Notice: Subject to any disclaimer, the term of this patent is extended or adjusted under 35 U.S.C. 154(b) by 0 days.

(21) Appl. No.: 14/554,840

(22) Filed: Nov. 26, 2014

(65) Prior Publication Data
US 2015/0087973 A1  Mar. 26, 2015

Related U.S. Application Data

(60) Continuation-in-part of application No. 14/311,464, filed on Jun. 23, 2014, now Pat. No. 9,017,729, which is a continuation-in-part of application No. 13/915,282, filed on Jun. 11, 2013, now Pat. No. 8,932,636, which is a continuation-in-part of application No. 13/665,458, filed on Oct. 31, 2012, now Pat. No. 8,668,935, which is a continuation-in-part of application No. 13/610,503, filed on Sep. 11, 2012, now Pat. No. 8,709,488, which is a continuation-in-part of application No. 13/527,005, filed on Jun. 19, 2012, now Pat. No. 8,795,251, which is a continuation-in-part of application No. 13/455,237, filed on Apr. 25, 2012, now Pat. No. 8,808,268, which is a continuation-in-part of application No. 13/361,786, filed on Jan. 30, 2012, now Pat. No. 8,801,690, which is a continuation-in-part of application No. 13/307,916, filed on Nov. 30, 2011, now Pat. No. 8,481,082, which is a continuation-in-part of application No. 13/189,606, filed on Jul. 25, 2011, now Pat. No. 8,119,165, which is a continuation-in-part of application No. 13/149,209, filed on May 31, 2011, now Pat. No. 8,137,698, which is a continuation-in-part of application No. 12/478,029, filed on Jun. 4, 2009, now Pat. No. 7,964,214, which is a continuation-in-part of application No. 11/485,352, filed on Jul. 13, 2006, now Pat. No. 7,638,139, which is a division of application No. 10/073,863, filed on Feb. 14, 2002, now Pat. No. 7,101,571.

(51) Int. Cl.
| | | |
|---|---|---|
| *A61K 41/00* | (2006.01) | |
| *A61K 47/48* | (2006.01) | |
| *A61K 45/06* | (2006.01) | |
| *A61B 5/00* | (2006.01) | |
| *A61F 9/00* | (2006.01) | |
| *A61B 18/04* | (2006.01) | |
| *A61F 7/00* | (2006.01) | |
| *A61N 2/00* | (2006.01) | |
| *A61N 5/10* | (2006.01) | |
| *A61B 3/13* | (2006.01) | |
| *A61N 7/02* | (2006.01) | |
| *A61K 49/22* | (2006.01) | |
| *A61K 9/00* | (2006.01) | |
| *A61K 9/127* | (2006.01) | |
| *A61B 6/03* | (2006.01) | |
| *A61N 2/02* | (2006.01) | |
| *A61N 5/02* | (2006.01) | |
| *A61B 8/08* | (2006.01) | |
| *A61B 5/01* | (2006.01) | |
| *A61F 9/007* | (2006.01) | |
| *G01R 33/48* | (2006.01) | |
| *A61F 9/008* | (2006.01) | |

(52) U.S. Cl.
CPC ............... *A61K 41/0052* (2013.01); *A61B 3/13* (2013.01); *A61B 5/0095* (2013.01); *A61B 18/04* (2013.01); *A61F 7/00* (2013.01); *A61F 9/0008* (2013.01); *A61K 9/0009* (2013.01); *A61K 9/127* (2013.01); *A61K 45/06* (2013.01); *A61K 47/48569* (2013.01); *A61K 47/48861* (2013.01); *A61K 47/48884* (2013.01); *A61K 49/227* (2013.01); *A61N 2/002* (2013.01); *A61N 5/1001* (2013.01); *A61N 5/1017* (2013.01); *A61N 7/02* (2013.01); *A61B 5/01* (2013.01); *A61B 5/4839* (2013.01); *A61B 6/032* (2013.01); *A61B 6/037* (2013.01); *A61B 8/0841* (2013.01); *A61F 9/0079* (2013.01); *A61F 2009/00863* (2013.01); *A61N 2/004* (2013.01); *A61N 2/02* (2013.01); *A61N 5/025* (2013.01); *G01R 33/4808* (2013.01)

(58) Field of Classification Search
None
See application file for complete search history.

(56) References Cited

U.S. PATENT DOCUMENTS

| | | | |
|---|---|---|---|
| 3,993,754 | A | 11/1976 | Rahman et al. |
| 4,235,871 | A | 11/1980 | Papahadjopoulos et al. |
| 4,522,803 | A | 6/1985 | Lenk et al. |
| 4,586,512 | A | 5/1986 | Do-huu et al. |
| 4,620,546 | A | 11/1986 | Aida et al. |
| 4,658,828 | A | 4/1987 | Dory |
| 4,891,043 | A | 1/1990 | Zeimer et al. |
| 5,094,854 | A | 3/1992 | Ogawa et al. |
| 5,149,319 | A | 9/1992 | Unger |
| 5,203,782 | A | 4/1993 | Gudov et al. |
| 5,935,942 | A | 8/1999 | Zeimer |
| 5,976,502 | A | 11/1999 | Khoobehi et al. |
| 6,179,767 | B1 | 1/2001 | Ziegler et al. |

(Continued)

OTHER PUBLICATIONS

Andor Technology, "Transport Across the Nuclear Membrane Using Quantum Dots," Aug. 23, 2011, available at http://www.andor.com/company/news/?docID=1224.

(Continued)

*Primary Examiner* — Yunsoo Kim
(74) *Attorney, Agent, or Firm* — Thompson Hine LLP

(57) ABSTRACT

A method and composition for hyperthermally treating tumor cells in a patient under conditions that affect tumor stem cells and tumor cells.

16 Claims, 6 Drawing Sheets

(56) References Cited

U.S. PATENT DOCUMENTS

| | | | |
|---|---|---|---|
| 6,197,022 | B1 | 3/2001 | Baker |
| 6,248,727 | B1 | 6/2001 | Zeimer |
| 6,984,655 | B1 | 1/2006 | Mori et al. |
| 7,638,139 | B2 | 12/2009 | Peyman |
| 2002/0174743 | A1 | 11/2002 | Mukherjee et al. |

OTHER PUBLICATIONS

Boyden, "Optogenetics: Using Light to Control the Brain," The Dana Foundation, Nov. 30, 2011, available at http://www.dana.org/news/cerebrum/detail.aspx?id=34614.
Buchen, "Illuminating the Brain," Nature, vol. 465, May 6, 2010, pp. 26-28.
Dixit et al., "Quantum Dot Encapsulation in Viral Capsids," Nano Letters, vol. 6, No. 9 (2006); pp. 1993-1999.
Deisseroth, "Optogenetics," Nature Methods, Published online Dec. 20, 2010, available at http://www.stanford.edu/group/dlab/papers/deisserothnature2010.pdf.
Deisseroth, "Optogenetics: Controlling the Brain with Light [Extended Version]," Scientific American, Published online Oct. 20, 2010, available at http://www.scientificamerican.com/article.cfm?id=optogenetics-controlling.
Dubertret et al., "In vivo Imaging of Quantum Dots Encapsulated in Phospholipid Micelles," Science, vol. 298, No. 5599 (2002), pp. 1759-1762.
Gill et al., "Fluorescence Resonance Energy Transfer in CdSe/ZnS-DNA Conjugates: Probing Hybridization and DNA Cleavage," J. Phys. Chem. B., vol. 109 (2005), pp. 23175-23179.
Joo et al., "Enhanced Real-Time Monitoring of Adeno-Associated Virus Trafficking by Virus—Quantum Dot Conjugates," ACSNano, vol. 5, issue 5 (2011); pp. 3523-3535.
Michalet et al., "Quantum Dots for Live Cells, in Vivo Imaging, and Diagnostics," Science, 307, No. 5709 (2005), pp. 538-544.
Yizhar et al., "Optogenetics in Neural Systems," Neuron, vol. 71 (2011), 9-34.
Zhang et al., "Optogenetic interrogation of neural circuits: technology for probing mammalian brain structures," Nature Protocols vol. 5, No. 3 (2010), pp. 439-456.
Aguilera et al. "Systemic in vivo distribution of activatable cell penetrating peptides is superior to cell penetrating peptides," Integr Biol (Camb), vol. 1, No. 5-6 (2009), pp. 371-381.
Kelley. "What Clinicians Need to Know About Molecular Markers in Solid Tumors" Aug. 6, 2010, available at http://www.medscape.org/viewarticle/725989.
Nguyen et al. "Surgery with molecular fluorescence imaging using activatable cell-penetrating peptides decreases residual cancer and improves survival," Proc. Nat. Acad. Sci., vol. 107, No. 9 (2010), pp. 4317-4322.
Olson et al. "In vivo characterization of activatable cell penetrating peptides for targeting protease activity in cancer," Integr Biol, vol. 1 (2009), pp. 382-393.
Olson et al. "Activatable cell penetrating peptides linked to nanoparticles as dual probes for in vivo fluorescence and MR imaging of proteases," Proc. Nat. Acad. Sci. vol. 107, No. 9 (2010), pp. 4311-4316.
Heath et al. "Varying Polymer Architecture to Deliver Drugs," The AAPS Journal vol. 9, No. 2 (2007), Article 26.
Hoare et al. "A Magnetically-Triggered Composite Membrane for On-Demand Drug Delivery," Nano Lett., vol. 9, No. 10 (2009), pp. 3651-3657.
Mornet et al., Magnetic nanoparticle design for medical diagnosis and therapy, J. Mater. Chem., vol. 14 (2004), pp. 2161-2175.
Sexton et al. "A Protective Vaccine Delivery System for In Vivo T Cell Stimulation Using Nanoengineered Polymer Hydrogel Capsules," ACS Nano, vol. 3, No. 11 (2009), pp. 3391-3400.
Alavarez-Lorenzo et al., "Temperature-sensitive chitosan-poly(N-isopropylacrylamide) interpenetrated networks with enhanced loading capacity and controlled release properties" J. Controlled Release 102(3), (2005) 629-641.
Balasubramaniam et al., "Poly(N-isopropylacrylamide)-Coated Superaramagnetic Iron Oxide Nanoparticles: Relaxometric and Fluorescence Behavior Correlate to Temperature-Dependent Aggregation" Chem. Mater., 2011, 23, 3348-3356.
Benyettou et al., "Magnetoliposome for alendronate delivery" J. Mater. Chem., 2011, 21, 4813-4820.
Budgin et al. "Functionalization of Magnetic Nanoparticles with Amphiphilic Block Copolymers: Self-Assembled Thermoresponsive Submicrometer Particles" Langmuir, 2012, 28, 4142-4151.
Farokhzad et al., "Impact of Nanotechnology on Drug Delivery" ACS Nano 3(1) 2009, 16-20.
Filipa et al., "Polyelectrolyte-Coated Unilamellar Nanometer-Sized Magnetic Liposomes" Langmuir 2009, 25(12), 6793-6799.
Pothayee et al., "Magnetic Block Ionomer Complexes for Potential Dual Imaging and Therapeutic Agents" Chem. Mater. 2012, 24 2056-2063.
Tai et al. "Thermosensitive liposomes entrapping iron oxide nanoparticles for controllable drug release" Nanotechnology 20 (2009) 135101 (9 pages).
Xu et al. "Controlled Release and Assembly of Drug Nanoparticles via pH-Responsive Polymeric Micelles: A Theoretical Study" J. Phys. Chem. B, 2012,116 (20), 6003-6009.
Booth et al. Exosomes and HIV Gag bud from endosome-like domains of the T cell plasma membrane. *The Journal of Cell Biology*, vol. 172, No. 6, Mar. 13, 2006, 923-935.
Jarnagin et al. Treatment of cholangiocarcinoma with oncolytic herpes simplex virus combined with external beam radiation therapy. Cancer Gene Therapy 13 (2006) 326-334.
Ding et al. Farnesyltransferase inhibitor tipifarnib inhibits Rheb prenylation and stabilizes Bax in acute myelogenous leukemia cells. haematologica 99 (2014) 60-69.
Kleiner et al. Farnesyl and geranylgeranyl transferase inhibitors:an anti-inflammatory effect. Comment to "Inhibition of protein geranylgeranylation and farnesylation protects against graft-versus-host disease via effects on CD4 effector T cells" haematological 98 (2013) e44-e45.
Karp et al. Multi-institutional phase 2 clinical and pharmacogenomic trial of tipifarnib plus etoposide for elderly adults with newly diagnosed acute myelogenous leukemia. Blood 119 (2012) 55-63.
Hong et al. Phase I Trial of a Combination of the Multikinase Inhibitor Sorafenib and the Farnesyltransferase Inhibitor Tipifarnib in Advanced Malignancies. Clin Cancer Res 15 (2009), 7061-7068.
Kurzrock et al. Phase I Study of Alternate-Week Administration of Tipifarnib in Patients with Myelodysplastic Syndrome. Clin Cancer Res 14 (2008) 509-514.
Haferlach. Molecular Genetic Pathways as Therapeutic Targets in Acute Myeloid Leukemia. Hematology (2008) 400-411.
Armand et al. The Emerging Role of Targeted Therapy for Hematologic Malignancies: Update on Bortezomib and Tipifarnib. The Oncologist 12 (2007) 281-290.
Yanamandra et al. Tipifarnib and Bortezomib Are Synergistic and Overcome Cell Adhesion—Mediated Drug Resistance in Multiple Myeloma and Acute Myeloid Leukemia. Clin Cancer Res 12 (2006) 591-599.
Beaupre et al. R115777 induces Ras-independent apoptosis of myeloma cells via multiple intrinsic pathways. Mol Cancer Ther 3 (2004) 179-186.

The electromagnet can be converted also to an alternating magnet.

All patients can be treated with an alternating magnet, electromagnetic radiation or ultrasound.

METHOD AND COMPOSITION FOR HYPERTHERMALLY TREATING CELLS

This application is a Continuation-in-Part of co-pending U.S. patent application Ser. No. 14/311,464 filed Jun. 23, 2014; which is a Continuation-in-Part of U.S. patent application Ser. No. 13/915,282 filed Jun. 11, 2013; which is Continuation-in-Part of U.S. patent application Ser. No. 13/665,458 filed Oct. 31, 2012 now U.S. Pat. No. 8,668,935; which is a Continuation-in-Part of U.S. patent application Ser. No. 13/610,503 filed Sep. 11, 2012 now U.S. Pat. No. 8,709,488; which is a Continuation-in-Part of co-pending U.S. patent application Ser. No. 13/527,005 filed Jun. 19, 2012; which is a Continuation-in-Part of co-pending U.S. patent application Ser. No. 13/455,237 filed Apr. 25, 2012; which is a Continuation-in-Part of co-pending U.S. patent application Ser. No. 13/361,786 filed Jan. 30, 2012; which is a Continuation-in-Part of co-pending U.S. patent application Ser. No. 13/307,916 filed Nov. 30, 2011 now U.S. Pat. No. 8,481,082; which is a Continuation-in-Part of U.S. patent application Ser. No. 13/189,606 filed Jul. 25, 2011 now U.S. Pat. No. 8,119,165; which is a Continuation-in-Part of U.S. patent application Ser. No. 13/149,209 filed May 31, 2011 now U.S. Pat. No. 8,137,698; which is a Continuation-in-Part of U.S. patent application Ser. No. 12/478,029 filed Jun. 4, 2009 now U.S. Pat. No. 7,964,214; which is a Continuation-in-Part of U.S. patent application Ser. No. 11/485,352 filed Jul. 13, 2006 now U.S. Pat. No. 7,638,139; which is a Division of U.S. patent application Ser. No. 10/073,863 filed Feb. 14, 2002 now U.S. Pat. No. 7,101,571; the entirety of each is hereby expressly incorporated by reference herein.

FIELD OF THE INVENTION

The present invention relates to a method and composition for hyperthermally treating cells at a site in the body. More particularly, the present invention relates to a method for treating cells at a target site in the body, such as at a lens capsule of an eye, tumors, and exudative or wet age related macular degeneration (AMD) by applying thermal energy to the target site to heat the cells to a temperature which will kill the cells or impede cell multiplication without exceeding the protein denaturation temperature of the tissue.

BACKGROUND OF THE INVENTION

Several techniques currently exist for treating cells at a selected site in the body with heat or chemicals to kill or impede multiplication of those cells to prevent undesired cell proliferation. For example, numerous types of chemotherapy drugs exists which, when injected into a tumor or delivered systemically to a patient, attack and kill cancerous cells to prevent them from further multiplying. However, unless the treatment affects the tumor stem cells that have mutated to result in uncontrolled tumor growth and metastasis, treatment will not be effective. Stem cells are pluripotential undifferentiated cells. Tumor stem cells are frequently located in the bulk tumor mass, are involved in tumor metastasis, and often elude detection. Over time, stem cells become resistant to standard chemotherapy regimens by constant genetic mutations that confer resistance.

Thermal radiation techniques can also be used to kill cancerous or other undesired cells. Cell death begins to occur when the cells are heated to a temperature of about 5° C. or more above the normal body temperature of 37° C. Applying thermal radiation to a localized site in the body, such as a tumor or other area containing undesired cells, can heat the cells at the site to temperatures in excess of 60° C. Such high temperatures causes a phenomenon known as protein denaturation to occur in the cells, which results in immediate cell death. Accordingly, thermal radiation therapy has been suitable in successfully treating certain types of cancers and other diseases involving uncontrolled cell growth.

Other types of heating techniques, such as the use of probes or catheters to provide localized heat to a site of interest also exist. Like thermal radiation therapy, these techniques also heat the cells to a temperature sufficient to cause protein denaturation in the cells to thus kill the cells quickly.

Photosensitive chemicals are also used to kill cells at certain sites of interest in the body. For example, a photosensitive chemical can be injected directly into a site of interest to expose cells at that site to the chemical. A light emitting source, which emits light at a wavelength that will activate the photosensitive chemical, is then focused on the site of interest. Accordingly, the light activates the photosensitive chemical that has been absorbed by or is otherwise present in the cells of interest. The activated chemical kills the cells, which thus prevents undesired cell proliferation.

Although the techniques mentioned above can be suitable for preventing certain types of cell proliferation at certain sites in the body, several drawbacks with these techniques exist. For example, often the use of chemotherapy drugs alone to treat a tumor or cancerous site is insufficient to kill the undesired cells. The only current treatments directed at tumor stem cells are heavy doses of ionizing radiation, thermal radiation or thermotherapy, or chemotherapy. Moreover, the chemotherapy drugs and other treatments also indiscriminately kill many normal healthy cells along with the cancerous cells, which can adversely affect the patient's health and are frequently ineffective against late stage cancers.

The use of ionizing radiation in conjunction with chemotherapy can have a more detrimental effect on the cancerous cells. However, as with chemotherapy, ionizing radiation often kills normal healthy cells, such as those in front of or behind the site of interest, along with the cancerous cells. Moreover, the intense heating of the cells can cause the cells to coagulate and thus block the capillaries at the site of interest. The blocked capillaries therefore prevent chemotherapy drugs from reaching the site of interest.

One example of a method of chemically treating a target site is disclosed in U.S. Pat. No. 6,248,727 to Zeimer. This method delivers a liposome containing a fluorescent dye and tissue-reactive agent. The liposome is administered intravenously to flow to the locus in the eye of the patient and the site is non-invasively heated to release the dye and the tissue-reactive agent. The dye is fluoresced to observe the pattern of the fluorescence. The tissue-reactive agent is activated to chemically damage and occlude the blood vessel. The liposomes are selected to release the dye at a temperature of 41° C. or less without causing thermal damage to the blood vessel.

In addition, the above techniques have not been used to prevent unwanted cell proliferation at certain locations in the eye, such as at the retina or at the lens capsule. Because the retina is very sensitive, conventional ionizing radiation techniques can be too severe to treat cancerous cells on, in or under the retina.

Also, after cataract surgery, a phenomenon known as capsular opacification and, in particular, posterior capsular opacification can occur in which the epithelial cells on the lens capsule of the eye experience proliferated growth. This growth can result in the cells covering all or a substantial portion of the front and rear surfaces of the lens capsule, which can cause the lens capsule to become cloudy and thus adversely affect the patient's vision. These cells can be removed by known techniques, such as by scraping away the epithelial cells. However, it is often difficult to remove all of the unwanted cells. Hence, after time, the unwanted cells typically will grow back, thus requiring further surgery.

Accordingly, a need exists for a method for hyperthermally treating tissue and preventing unwanted cell proliferation at sites in the body, especially at sites in the eye such as the retina, choroid and lens capsule, which does not suffer from the drawbacks associated with the known techniques discussed above. The method should also treat tumor stem cells to target and eradicate a tumor source and eliminate or slow tumor metastasis. The method should also target and damage the specific tumor-associated vasculature, in effect, starving the tumor of its nutrient supply.

SUMMARY OF THE INVENTION

The present invention is directed to a method of hyperthermally treating tissue by heating the tissue above a temperature which kills cells in the tissue. In particular, the invention is directed to a method of heating tissue above a temperature effective to treat the tissue without denaturing the protein. The present invention also relates to a method and composition for hyperthermally treating cells in the eye with simultaneous imaging.

One embodiment of the method targets tumor stem cells by combining chemotherapy with thermotherapy to target tumor stem cells while leaving normal cells either unaffected or minimally effected by the therapy. This embodiment of the method uses increases in temperature to first prime the tumor stem cells, and then to kill the tumor stem cells synergistically with thermotherapy. In one embodiment, nanoparticles that are coated with or otherwise contain antibodies that specifically target certain cells and/or cell types, e.g., tumor cells. This helps to minimize or eliminate chemotherapy adverse effects on non-tumor bearing vital organs such as liver, kidney, gut, heart, central nervous system, while providing supra-therapeutic doses of the chemotherapy drugs to tumor cells, both local and metastatic, and stem cells. In this way, the duration of chemotherapy administered to a patient may be reduced without compromising effective treatment.

One embodiment of the method targets tumor stem cells by combining localized internal ionizing radiation therapy with thermotherapy to target tumor stem cells and to destroy their associated vasculature, while leaving normal cells and non-tumor vasculature either unaffected or minimally affected by the therapy. This embodiment of the method uses increases in temperature to first prime the tumor stem cells, and then to kill the tumor stem cells synergistically with thermotherapy, and uses localized internal ionizing radiation therapy to destroy vasculature associated with the tumor. In one embodiment, nanoparticles that are coated with or otherwise contain antibodies that specifically target certain cells and/or cell types, e.g., tumor cells, also contain a radioactive isotope. The increased temperature from the thermotherapy kills the tumor stem cells, both local and metastatic. The localized internally administered radiotherapy damages the proximate and/or adjacent endothelial cells of the vasculature feeding the tumor cells, both local and metastatic. The embodiment of the method may be used in a patient receiving anti-vascular endothelial growth-factor therapy to provide an additional source of vessel damage. This combination therapy increases the likelihood of eradication of tumor cells and stem cells associated with the tumor by additionally damaging or obliterating the vessels that provide their nutrient supply. The result is more robust therapy and increased chances for patient survival.

Accordingly, a primary aspect of the invention is to provide a method for heating tissue at least to a temperature sufficient to hyperthermally treat the tissue.

Another aspect of the invention is to provide a method of hyperthermally treating tissue to a temperature sufficient to kill cells in the tissue and at a temperature below the protein denaturization temperature of the tissue.

A further aspect of the invention is to provide a method of hyperthermally treating tissue, where the tissue includes or is provided with a temperature indicator to indicate a hyperthermally effective temperature of the tissue.

Still another aspect of the invention is to provide a method of hyperthermally treating tissue where a temperature indicator composition is introduced into the tissue or bloodstream near the tissue to indicate a tissue temperature effective to hyperthermally treat the tissue and a temperature indicator to indicate a tissue temperature above a protein denaturization temperature of said tissue.

A further aspect of the invention is to provide a method of hyperthermally treating tissue by introducing a temperature indicator into the tissue and heating the tissue to a temperature where the temperature indicator can be detected. In a preferred embodiment, the temperature at which the indicator can be detected is a temperature effective to hyperthermally treat the tissue and is at a temperature below the protein denaturization temperature.

A further aspect of the invention is to provide a method of heating and detecting a temperature of a tissue between a first temperature and a second temperature. The method introduces a temperature indicator into the tissue. The temperature indicator includes a first dye that can be detected at the first temperature to indicate that the first temperature has been reached, and a second dye that can be detected at the second temperature to indicate that the second temperature has been reached.

Still another aspect of the invention is to provide a temperature indicating composition for introducing into a tissue to be thermally treated. The composition includes a first dye encapsulated in a heat sensitive liposome where the first dye is releasable at a temperature effective to hyperthermally treat the tissue and at a temperature below the protein denaturization temperature. The composition also includes a second dye encapsulated in a second liposome where the second dye is releasable at a temperature at or above the protein denaturization temperature.

Another aspect of the invention is to provide a method to hyperthermally treat tissue to kill the tissue cells substantially without protein denaturization of the tissue where the tissue includes a heat sensitive liposome containing a temperature indicating dye and a temperature activated bioactive compound. The tissue is heated to release the dye from the liposome to indicate a thermally effective temperature to kill cells in the tissue at a temperature below the protein denaturization temperature. The heat applied to the tissue simultaneously releases the bioactive compound to treat the tissue.

Another aspect of the invention is to provide labeled nanoparticles, either alone or conjugated with activatable cell-penetrating peptides (ACPPs) to assist in localizing and destroying cancer cells or tumor tissue remaining after surgical excision of a tumor. Another aspect of the invention relates to ACPP-conjugated nanoparticles that can also be adapted to attach to normal cell specific receptors in order to stain and treat the tissues. These cells can be as involved with vasculature such as myofibroblasts becoming activated after stent surgery; or nerve cells that create neuromas. Another aspect of the invention relates to the treatment or debulking of other unwanted masses, such as fibromas, meningiomas, adenomas, or degenerative cells causing Parkinson's Disease or of nerves involved in transmitting pain, e.g., for patients in chronic pain. Another aspect of the invention is to treat malignant tumors, such as neuroblastoma, melanoma, skin, breast, brain kidney, lung, intestinal, and genitourinary, bone, gland, and blood cancers. Another aspect of this invention is to target normal cells of the body responsible for an immune response, such as lymphocytes, etc., that prevent an organ transplant. Another aspect of the invention is to treat undesirable vascular rupture and bleeding.

Another aspect of the invention is to target and damage tumor cells, tumor stem cells, and endothelial cells of tumor-associated vessels, e.g., blood vessels, lymphatics.

Another embodiment of the invention is to provide immunotherapy in combination with thermal therapy to a target site. Thermotherapy is provided by administering a composition comprising a targeting agent and/or antitumor-antibody-labeled nanoparticle where the nanoparticle forms a targeting agent and/or antibody labeled nanoparticle-cell complex at a tumor site, exposing the patient to an energy source where the nanoparticles respond by expanding thus generating an acoustic signal, measuring the acoustic signal and relating the measured signal to a temperature of the nanoparticle-cell complex, and controlling the temperature of the nanoparticle-cell complex from about 39° C. to about 58° C. based on the acoustic signal to hyperthermally damage or kill cells in the tumor; and providing immunotherapy by providing an immunotherapy agent associated with the nanoparticles, providing an immunotherapy agent not associated with the nanoparticles, and/or providing a therapeutic concentration of autologous leukocytes to the patient, where immunotherapy enhances a patient's immune response. In specific embodiments, thermotherapy is performed in the absence of a contrast agent, substantially simultaneously with, prior to, or subsequent to immune therapy. The immunotherapy may reduce immunosuppression. The thermotherapy may supplement chemotherapy and/or radiation therapy. A marker may be evaluated to assess a therapy effect. The nanoparticle may be associated with a member of specific binding pair such as streptavidin-biotin pair, a cellular receptor-agonist or antagonist pair, an enzyme-substrate pair, and/or an antibody-antigen pair. The nanoparticle may be associated with a virus, e.g., a modified virus, a tumoricidal virus, and/or an adeno-associated virus (AAV).

The various aspects of the invention are basically attained by providing a method of hyperthermally treating tissue in an animal. The method comprises the step of introducing a temperature indicating substance into the bloodstream of the animal to flow through a target site. The temperature indicating substance includes a fluorescent dye encapsulated within a heat sensitive liposome. The fluorescent dye is releasable from the liposome at a temperature of at least 41° C. A heat source is applied to the target site and the target is hyperthermally heated to at least 41° C. to release and fluoresce the dye and to hyperthermally treat the target site for a time sufficient to kill cells in the tissue.

The aspects of the invention are also attained by providing a method of detecting a threshold temperature and of hyperthermally treating tissue in an animal. The method comprises the step of introducing a first fluorescent dye encapsulated in a first heat sensitive liposome into the bloodstream of an animal in a location to flow through a target site in the animal. The first fluorescent dye is releasable from the first heat sensitive liposome at a temperature of at least 41° C. The target site is heated to a temperature to release the first fluorescent dye and the first fluorescent dye is fluoresced to indicate and visualize a tissue temperature of at least 41° C. Heating of the target site is continued at a temperature of at least 41° C. for a time sufficient to hyperthermally treat the tissue.

Another aspect of the invention is a method of targeting tumor stem cells for therapy in a patient needing the therapy, e.g., a cancer patient either simultaneously undergoing chemotherapy or having previously undergone chemotherapy. The method administers chemotherapy with thermotherapy, with thermotherapy being a stepwise increase in temperature that, at relatively lower temperatures, primes the tumor cells, including tumor stem cells, for increased susceptibility to the chemotherapy. Then at relatively higher temperatures, the method kills the primed tumor stem cells with a synergistic combination of the chemotherapy and the thermotherapy.

Another aspect of the invention is a method of targeting tumor cells, tumor stem cells, and endothelial cells of tumor-associated vessels to selectively destroy both the tumor as well as the vessels feeding the tumor by combining thermal therapy with localized internally administered ionizing radiation therapy.

The aspects of the invention are further attained by providing a method of hyperthermally treating tissue of an animal. The method comprises the step of introducing a temperature indicating substance into the bloodstream of the animal to flow through a target site. The temperature indicating substance includes a first fluorescent dye encapsulated in a first temperature sensitive liposome. The first fluorescent dye is releasable from the first liposome by heating to a temperature of at least 42° C. A second fluorescent dye encapsulated in a second temperature sensitive liposome is also included. The second fluorescent dye is releasable from the second liposome by heating to a temperature of at least 50° C. The target site is heated to a temperature of at least 42° C. The first fluorescent dye is fluoresced to indicate an effective temperature for hyperthermally treating the tissue without releasing the second fluorescent dye from the second liposomes.

Another aspect discloses a method of delivering particulate material, e.g., nanoparticles, into mammalian cells and/or tumor cells through pinocytic uptake and/or using various channels. In one embodiment, the particulate material is delivered to the nuclear membrane, which typically has a pore size <100 nm in diameter. In one embodiment, the pores and/or pinocytic vesicles etc. permit the nanoparticles, smaller than 100 nm, to be taken up into the cytoplasm or the nucleus of the cells/bacteria. The nanoparticles are coated with or contain an antibody and/or drug. The non-magnetic and/or magnetic nanoparticles, once taken up by the cell/bacteria, are heated selectively by an external source such as electromagnetic energy or a reversible magnetic field, and imaged using either a photoacoustic technology or MRI.

These and other aspects of the invention will become apparent to one skilled in the art in view of the following detailed description of the invention.

DETAILED DESCRIPTION OF THE INVENTION

Figure 1:
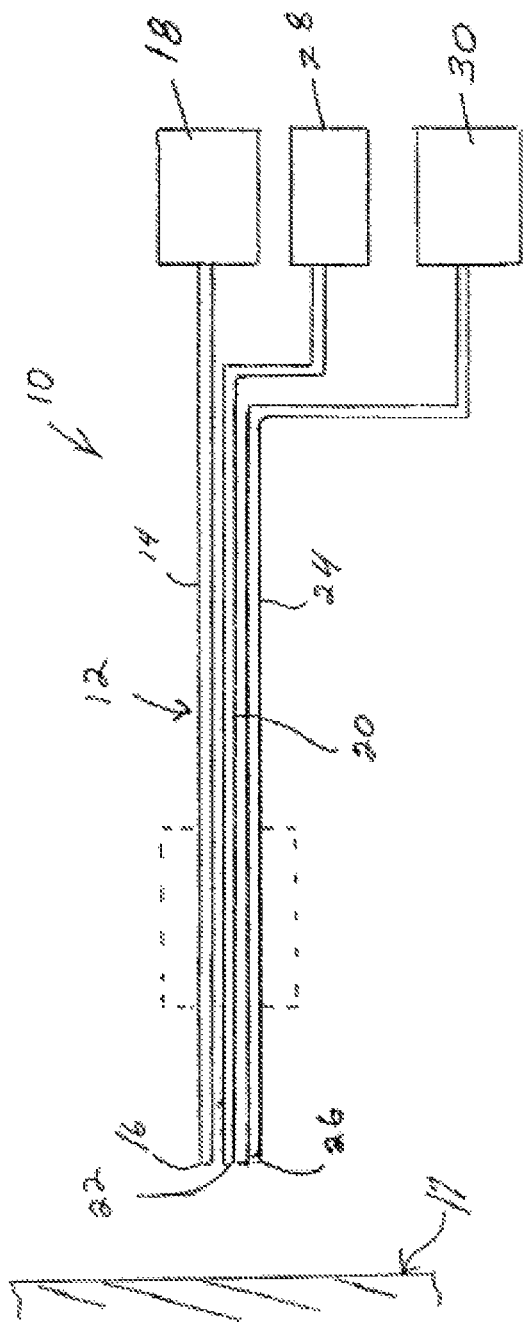
FIG. 1 is a schematic diagram of one embodiment of the invention showing a probe for hyperthermally treating tissue and visualizing a dye in the target site.

The present invention is directed to a method and composition for hyperthermally treating tissue. In particular, the invention is directed to as method for heating tissue above a temperature effective to kill tissue cells or inhibit multiplication of cells below the protein denaturization temperature of the tissue.

The method of the invention introduces a composition into the bloodstream or other system of the body in a location to flow into or through a target site to be treated. In one embodiment, the composition is introduced into the lymphatic system. A heat source such as generated by radiation energy is applied to the target site to heat the tissue in the target site for a time sufficient to hyperthermally treat the tissue and activate the composition. As used herein, the term "hyperthermal" refers to a temperature of the cell or tissue that kills or damages the cells without protein denaturization.

The composition may contain a temperature indicator that is able to provide a visual indication when a minimum or threshold temperature is attained that is sufficient to hyperthermally treat the tissue. It is a feature of the invention to provide a method of heating tissue in a target site to a hyperthermally effective temperature and to provide a visual indication that a temperature of at least 41° C., and preferably at least 42° C. is attained. In one embodiment, the composition includes a second temperature indicator to provide a visual indication when a protein denaturization temperature is attained thereby providing an indication that a maximum desired temperature is exceeded. The heat source can be applied to the tissue so that the composition provides an indication that a thermally effective temperature is attained that is below the protein denaturization temperature of the tissue.

In one embodiment of the invention, the method introduces a composition to a target site, where the composition includes a fluorescent dye that is encapsulated in a heat sensitive particle, such as a liposome. The dye is a fluorescent dye that can be excited to fluoresce and be observed or visualized by the operator. Preferably, the heat sensitive liposomes are formed to rupture or release the fluorescent dye at a temperature at least equal to the temperature necessary to kill cells in the tissue and at a temperature below the protein denaturization temperature. The composition containing the heat sensitive liposomes encapsulating the fluorescent dye is introduced into the bloodstream to flow to or through the target site. The amount of the liposome composition is introduced in an amount effective to be released in or near the target site and to excited and visualized by the exciting light source and the visualizing device. The composition containing the dye can be injected in a single dose into the bloodstream or injected continuously to supply a continuous flow of the composition through the target site. The amount of the composition introduced can vary depending on the target site and the length of time that the dye is to be excited. A light or energy source is continuously applied to the target site to excite the dye and to cause the dye to fluoresce when released from the liposomes. An imaging device is used to capture the fluorescing light from the dye to provide a visual indication that the dye is released. The release temperature of the liposomes are selected to release the dye at a predetermined temperature so that when the dye is fluoresced and visualized, the visualization provides the operator with an indication that the release temperature in the target site has been attained. In one embodiment, the liposome composition is injected into the blood stream so that the composition is able to provide a continuous supply of the dye for fluorescing during the hyperthermal treatment. In this manner the operator is provided with a continuous indication that a sufficient temperature is being maintained.

The method of the invention is primarily directed to a method of heating tissue and cells in the tissue of an animal, particularly a human patient, at least to the temperature sufficient to kill or damage the cells. Cell death or cell damage is known to occur when the tissue cells are heated to a temperature of about 5° C. above the normal body temperature of 37° C. Therefore, the method of the invention heats the cells in the tissue to a temperature of about 41° C., and preferably at least 42° C. for a time sufficient to kill or damage the cells. Preferably, the heat source is applied to minimize unnecessary damage to the surrounding cells and tissue.

In one embodiment of the invention, the tissue is heated to a temperature of at least 41° C. and preferably in the range of at least about 42° C. to about 50° C. Heating the tissue to at least 42° C. ensures that a sufficient temperature is obtained to thermally treat the tissue and the cells effectively. Preferably, the tissue is heated to a temperature below the protein denaturization temperature of the tissue. Protein denaturization begins to occur at about 50° C. to 51° C. and occurs rapidly at temperatures of about 60° C. Preferably, the tissue is heated to a temperature of less than 60° C. and more preferably to a temperature of about 50° C. or less.

In one preferred embodiment, the tissue and the cells are heated to a temperature of about 47° C. to about 49° C. for a time sufficient to kill or damage the cells without protein denaturization. The length of time that the tissue is heated will depend on the location of the target site, the size and dimensions of the target site, the desired depth of penetration of the heat and the desired extent of thermal treatment- or damage of the tissue and cells in the target site. Typically, the heat source is applied for several minutes. In one embodiment, the heat source is applied for about 1 to 15 minutes, and typically about 5 to 10 minutes.

The heat source can be applied to a variety of the areas in the body where the hyperthermal treatment is desired. The target site can be tumors, organs, muscles and soft tissue. Examples of a target site include blood vessels and arteries, esophagus and eyes. In one embodiment, the method is suitable for hyperthermally treating the epithelial cells on the lens of the eye after cataract surgery. Other target sites include the retina and the choroid.

In other embodiments the target site may be cell components of various organs. The organs may be healthy or may contain tumors, either malignant or benign. The following are representative, not limiting, examples of cell components on which the inventive method may be applied: tumors of the central nervous system (CNS), various layers of skin and its underlying support structures, intestinal tract, kidney, urinary tract, female and male reproductive system organs, bone including bone marrow, circulatory system components including the heart, blood vessels, and circulating malignant cells, the lymphatic system including lymph nodes and vessels, and the respiratory system.

In one embodiment, the compositions including, e.g., gold or ferromagnetic nanoparticles, as described below, are injected through the nipple. The injected composition travels through the duct leading down from the nipple ending in glands, i.e., acini aggregated into lobules. This mode of injection may also introduce the composition into the lymphatic system, particularly if injected into the breast stroma. This embodiment may be used to treat breast cancer, as well as cancers in the associated lymphatic tissue. In addition, this embodiment may be used as a prophylactic treatment to obliterate or substantially reduce the breast glands' secretary epithelium in patients who exhibit genetic predisposition to breast cancer.

In various embodiments, the described compositions are introduced through any accessible cavity, such as oral, respiratory, or genitourinary cavities. The compositions may be introduced by needle injection or via a catheter. In one embodiment, the described methods may be used to treat cervical or bladder cancer, including early stages of the diseases.

In one embodiment, cell proliferation in tumors that would otherwise be excised from a body surface or removed from an internal body site are treated by the inventive method. Treatments involves both amelioration and/or tumor debulking, i.e., reducing the tumor mass. In one embodiment, the inventive method is used to augment surgical removal of a tumor. Tumors that are relatively large are often surgically removed, even if the tumor is determined to be non-malignant, because of the space-occupying nature of the tumor and/or the stress on other organs. For examples, stress on adjacent organs, such as liver and kidneys, can result in the potential for hepatic and nephrotic complications.

During surgical tumor excision or removal, it is important to ensure the tumor is completely removed, yet the tumor margins are difficult to recognize and determine. Typically, complete tumor removal requires multiple biopsies, during the surgical procedure itself and while the patient is under anesthesia, from the edges of the tumors. The biopsies are histologically or otherwise evaluated in real time by a pathologist. This very time consuming task prolongs surgery, may put the patient at increased risk, and definitive pathology results may take hours to obtain. Often, even after careful excision of the tumor, subsequent histologic studies of the entire lesion show that not all margins or edges are free of tumor tissues, resulting in patient anxiety, increased cost for subsequent surgery, and heightened risk of post-surgical complications. Such uncertainty of complete tumor and/or cancer cell removal makes subsequent medical treatment difficult to determine, e.g., whether to remove lymph nodes located in the area of the tumor, etc.

Malignant tumors have a preferred location in the body from which they grow from the initial mother cell. They then metastasize in other organs. The initial tumors are seen in any organ of the body (e.g., eye, brain, skin from which retinoblastomas, gliomas, melanomas occur; also prostate, colon and other intestinal tumors, pancreas, thyroid, etc. Tumors can grow from any type of tissue (e.g., ectoderm, mesoderm, endoderm, neuro-ectoderm). Using the eye as one example, melanomas can originate from the uveal tract, conjunctiva, orbit, etc. Melanomas of the choroid, ciliary body, and iris grow very slowly, in contrast to cutaneous melanomas, and remain in place before metastasizing. More rapidly growing melanomas preferentially metastasize in the liver, but are not limited and may metastasize to any organ. Prostate cancer preferentially metastasizes to bone. Colon cancer preferentially metastasizes to liver. Some tumors, such as basal cell carcinoma, gliomas, meningioma, etc. grow locally but damage vital organs.

It is thus desirable to treat the early diagnosed tumors locally and with a more intense therapy such as using ferromagnetic nanoparticles, with or without a single or combination of drugs, that can be attracted to a locally positioned magnet, either external or internal. Placement of a naturally occurring magnet or electromagnet, with a stable magnetic field, adjacent to or over the tumor area attracts and concentrates the circulating ferromagnetic particles to that specific location during their circulation in the blood after administration (e.g., injection) into the circulatory system, body cavity, etc., or at the site of administration, e.g., when topically applied to the skin, mucosa, etc.

In this embodiment, using a magnet to localize ferromagnetic particles at a tumor or lesion site, or even using whole body therapy, thermotherapy is controllably applied to a patient to treat a localized tumor and metastasized lesions.

Activatable cell-penetrating peptides (ACPPs) that are labeled with fluorescent polycationic cell-penetrating peptide (CPP) coupled by a cleavable linker to a neutralizing peptide have been developed and utilized to visualize tumors during surgery. Similarly there are other tumor specific biomarkers that are known to one skilled in the art, used for breast tumor, genitourinary tumors, lung tumors, head and neck tumors, gastrointestinal tumors, brain tumors, etc., as only one non-limiting example, disclosed at http://www.medscape.org/viewarticle/725989. ACPP conjugated to dendrimers (ACP-PDs) and gadolinium chelates can allow MRI visualization of whole body tumors, permitting thermotherapy if the magnetic or gadolinium nanoparticles are labeled with ACPPD. However, gross observation of a labeled tumor does not guarantee that all the tumor margins will be visible or will removed. One reason is that tumor margins may contain sparse numbers of dispersed cancerous cells. Another reason is that cancerous cells may be embedded more deeply in the tissue and thus not amenable to labeling (e.g., staining) and/or visualization. Thus, while such a method helps the surgeon during a surgical procedure, it does not eliminate the need for a biopsy from the tumor margin or edge.

The inventive method provides safe surgical debulking of a large tumor, while concomitantly providing that the tumor margins or edges are free of viable cancerous cells, or that such cancerous cells are non-viable. The method removes and treats non-malignant tumors, damaged cells such as nerve cells, or normal cells involved in or affected by adverse immune reactions in organ transplant procedures.

One embodiment is a composition of a nanoparticle that is conjugated to an ACPP. The nanoparticle may be cleavably conjugated to the ACPP by, e.g., a linker (e.g., at least ethylene glycol moiety or a (poly)ethylene glycol moiety). In one embodiment, the nanoparticle is labeled with a label such as a fluorescent moiety, chemiluminescent moiety, etc. In one embodiment, the ACPP is labeled with a polycationic cell-penetrating peptide (CPP).

In one embodiment of the method, the above-described composition is prepared with any biocompatible excipient and is administered to a patient. In one embodiment, a regimen of low dose medication is prescribed to enhance the therapeutic effect of the inventive method including but not limited to at least one antiproliferative agent, e.g., cisplatin, carboplatin, tetraplatin, iproplatin, adriamycin, mitomycin C, actinomycin, ansamitocin and its derivatives, bleomycin, Ara-C, daunomycin, metabolic antagonists such as 5-FU, methotrexate, isobutyl 5-fluoro-6-E-furfurylideneamino-xy-1,2,3,4,5,6 hexahydro-2,4-dioxopyrimidine-5-carboxylate, melpharan, mitoxantrone, lymphokines, etc.

One embodiment provides a method of drug delivery and thermal damage to a target in a patient in need thereof. This embodiment provides four ranges of thermotherapy at the target site. The target may be a particular site in the body, e.g., a tumor site. The target may be an organism, e.g., a bacterial target. Each temperature range results in a specific effect, as subsequently described. The overall result of this embodiment is specific drug delivery and specific thermal treatment of the target.

This embodiment is based on the knowledge that pores in bacterial membrane increase specifically during bacterial cell growth. Pores can serve as a conduit for transfer of genes and plasmid DNA from other bacteria that can effect cell survival, e.g., render the bacteria drug-resistant. Bacteria can be engineered to produce proteins, e.g., insulin, by transmitting the genes encoding such proteins to the bacteria interior. One skilled in the art appreciates that the pore size and number of pores increase with a cell temperature increase in the range of about 2° C. to about 28° C. At a temperature of greater than about 40° C., bacteria become very vulnerable, e.g., they become particularly sensitive to drugs and frequently die. While the same mechanisms take place in mammalian cells, mammalian uptake occurs more by pinocytosis.

One embodiment is a method to target therapy in a patient in need thereof. An antibody-coated and/or drug-containing nanoparticle composition is administered to the patient, then stages of increasing temperature thermotherapy at the target containing the antibody specific and/or drug-coated nanoparticles are performed. In one embodiment, the target is imaged during the temperature increases. The thermotherapy is administered under conditions (e.g., temperatures, durations, etc.) sufficient to result in targeted therapy in the patient. The inventive method limits thermotherapy to a specific target, e.g., a tumor, bacteria, etc. and does not substantially affect normal cells proximate this target. In one embodiment, the method is performed on a patient receiving therapy, e.g., chemotherapy, radiation therapy, anti-vascular endothelial growth-factor therapy, and/or steroid therapy. In one embodiment, the anti-tumor antibody-coated or -containing nanoparticles further comprise a thermosensitive polymer which releases the drug contained in the nanoparticle by dissociation of the polymer when the thermosensitive temperature is attained. Thermosensitive polymers include chitosan-poly (N-isopropylacrylamide), smart polymers, poly(N-isopropylacrylamide (PNIPAM), poloxamers, poloxamines, and/or acid (PMA) polymers modified with thiol groups ($PMA_{SH}$).

In use, in one embodiment, the composition is administered to the patient with four subsequent staged increases in temperature. In one embodiment, the temperature at the target is first increased to result in drug release from the nanoparticles. These conditions typically occur with a temperature at the target of at least 35° C. to 43° C., which is provided for about 0.5 minutes to about 20 minutes. The temperature at the target is then increased to result in thermotherapy. These conditions typically occur with a temperature at the target of 43° C. to 50° C., which is provided for about 1 min to about 15 min. The temperature at the target is then increased to result in expansion of the gases that are dissolved in cellular fluids and concomitant expansion of the membrane, cytoplasm, and/or nuclear pores. Such expansion results in mechanical distension of the cell membrane and/or nuclear membrane with subsequent expansion of the membrane pores and/or channels allowing essentially unrestricted drug into the cell. These conditions typically occur with a temperature from 50° C. to 60° C., which is provided for about 1 min to about 10 min. The temperature at the target is then increased to result in water evaporation at the target, causing cumulative damage, i.e., essentially unrestricted drug flow combined with protein denaturation and water evaporation. These conditions typically occur with a temperature greater than 60° C. (i.e., a temperature that kills normal cells) and up to 100° C., which is provided for a duration less than one second to a few minutes.

As one example, in one embodiment, the composition is administered to the patient, then the temperature increase at the target is limited to less than 60° C. The tumor cells and/or bacterial cells, which are rapidly dividing and hence have increased susceptibility to increased temperature, are killed.

Thermotherapy may be provided by, e.g., electromagnetic radiation, ultrasound energy, or an alternating magnetic field. Imaging of the target during the temperature increases can control thermotherapy by connecting the photoacoustic system, which controls the heat generating systems, to the electromagnetic radiation-creating instrument, or to a reversible magnet, or another ultrasound system generating a focused ultrasound beam. This connection may be, e.g., by a processor. The operator instructs the system to achieve the desired temperature, or provides an algorithm for the system to follow to create the desired result, using specified temperatures and exposure durations. Imaging may be thermal imaging, photoacoustic imaging, X-ray imaging, optical coherence tomography, ultrasound imaging, fluorescence imaging, chemiluminescent imaging, positron imaging, surface enhanced Raman spectroscopy, and/or magnetic resonance imaging (MRI). In one embodiment, imaging is by MRI.

The composition administered may contain magnetic, diamagnetic, ferromagnetic, and/or paramagnetic nanoparticles. The composition administered may contain gold nanoparticles, diamond nanoparticles, platinum nanoparticles, and/or carbon nanoparticle.

The targeted nanoparticles, that contain antibody as well as drug in or on the particles, are administered to a patient in need thereof. The staged and selective temperature increases administered at the target deliver drug from the nanoparticle to the cell interior, with heat increasing metabolic need of the target (e.g., tumor cells or bacteria). Thermal therapy is staged as follows: a first temperature at the target site of at least 35° C. to 43° C., thereafter a second temperature at the target site of from 43° C. to 50° C., thereafter a third temperature at the target site of from 50° C. to 60° C., and thereafter a fourth temperature at the target site of greater than 60° C. The duration of the first stage is from 0.5 min to 20 min. The duration of the second stage is from 1 min to 15 min. The duration of the third stage is from 1 min to 10 min. The duration of the fourth stage is from less than 1 second to a few minutes. In embodiments, a stage of thermotherapy can be removed. For example, the method may be used in a patient with a tumor that is drug resistant, but the tumor will not be able to develop resistance to the increased temperature.

The inventive thermotherapy method results in specific drug delivery and thermal damage to target cells. The method delivers and releases drug from the nanoparticles to the cell interior. The increased temperature increases the tumor cell/bacteria metabolic needs. Without being bound by a specific theory, the result is cell damage and/or death by drug, by heat, or by the combination of drug and heat.

The staged, selective temperature increase in the nanoparticle can also expand the gas that are dissolved in the cell fluid, creating a mechanical stress/damage on the cells/bacteria membrane or internal metabolic machinery. The internal gas expansion distends the wall of the cell/bacteria and expands the pore size of the cell/bacteria membranes. This in turn causes almost free flow of drug to the cell interior, resulting in cell death. Increasing the temperature, while imaging, beyond 60° C. can also cause not only protein denaturation in the cell, but also cause the water molecules to evaporate. This further increases the cell damage leading to cell death. The different stages can be controlled by the imaging technology described controlling the thermal effect of the nanoparticles. The processes occur more rapidly and more readily (faster and sooner) around the nanoparticles than around the surrounding tissue because of the nanoparticles' small size.

Administration may be by any route and at body site. For example, the composition may be administered by an intrathecal, intravenous, intraocular, etc. route. The composition may be administered into a body cavity (e.g., eye, bladder). The composition may be administered into the cerebrospinal fluid. The composition may be applied topically, e.g., to an external or mucosal lesion. In one embodiment, the composition is intravenously administered. The composition may be administered locally in or near the tumor site, or in or at any body site.

The composition contains a nanoparticle conjugated to an activatable cell penetrating peptide (ACPP), which forms an antitumor-ACPP-nanoparticle-cell complex at the tumor tissue site, or target site (e.g., liver). The target site of the patient is exposed to an energy source under conditions sufficient to heat the nanoparticles in the antitumor-ACPP-nanoparticle-cell complex to a temperature that is sufficient to measure an acoustic response produced by the nanoparticle. Exemplary durations are from less than one second to 15 minutes. The treatment can be repeated as needed, e.g., within weeks, determined by MRI, CT, ultrasound, PET scans, etc.

In one embodiment, the temperature to measure an acoustic response produced by the nanoparticle, indicating damage to the target cells, ranges from about 40° C. to about 60° C. inclusive. A lower threshold temperature of 39° C. may be used with drug delivery to break up the medication-nanoparticle complex at the tumor site. In one embodiment, the temperature to measure an acoustic response produced by the nanoparticle, indicating damage to the target cells, ranges from about 42° C. to about 45° C. inclusive, or from about 45° C. to about 50° C. inclusive, or from about 50° C. to about 58° C. inclusive. In one embodiment, for superficially located or otherwise externally accessible tumors, or for treating tumor margins after surgical excision or debulking, a temperature >58° C. up to 60° C. is acceptable if the target is away, e.g. distal or remote, from a vital organ. Such hyperthermal therapy damages or kills the tumor cells, referred to as tumor de-bulking.

In one embodiment of the method, the tumor is surgically excised or removed prior to or concomitantly with administering the composition and performing the method. The surgery thus defines the lesion that is a target area for treatment by the method.

The method may be used on targets or lesions in and/or on any body site. Examples include, but are not limited to, skin, mucosa, organs and tissues of the digestive, genitourinary, nervous (CNS and/or peripheral nerves), respiratory, circulatory, lymphatic, and other systems. As one example, a tumor may be located in and/or on a mucosal lining or skin. As one example, cancerous blood cells may be treated by the inventive method, e.g., leukemia or lymphoma. In one embodiment, intravenous administration of the composition permits therapy to circulating blood or other cells (e.g., immune cells). With surgical tumor excision, the composition can be intravenously injected prior to, after, or during surgery.

In one embodiment, use of the method to eliminate specific immune cells effectively reduces or eliminates the need for immunosuppressive drugs in cases of organ transplant. In such an embodiment, nanoparticles are labeled with specific binding molecules that bind to specific surface receptors of these immune activated cells; the method proceeds as described. This embodiment minimizes or eliminates the need to expose the entire body to potentially damaging radiation, chemotherapy, and/or immunosuppressant medications, thus minimizing or eliminating their damaging side effects.

In one embodiment, use of the method combines hyperthermal treatment, as disclosed herein, with immunotherapy. The resultant immune-thermal therapy advantageously uses synergy from the combined approaches, specifically, (i) a patient's inherent response against a non-self substance, in this case a tumor cell, to destroy the tumor cell, and (ii) localized thermal therapy possible by using the inventive method with targeted directed nanoparticles.

Thermal therapy, also termed hyperthermal therapy, is completely described, disclosed, and enabled herein. All thermal therapy embodiments may be used in the inventive method.

In embodiments, thermal therapy may be performed simultaneously with, or substantially simultaneously with, immunotherapy. In embodiments, thermal therapy may be performed prior to immunotherapy. In embodiments, thermal therapy may be performed subsequent to immunotherapy. Because thermal therapy is targeted, involves thermal treatment without destroying proteins, and spares non-targeted tissue, it is generally relatively safer and less invasive than chemotherapy and/or radiation therapy.

Targeted therapy includes, but is not limited to, anti-tumor antibodies, other specific binding compounds known in the art such as biotin with streptavidin, specific receptors and receptor agonists and/or antagonists, etc. Targeted therapy may result when the nanoparticles contain and/or are coated with one part of the associated pair and the tumor itself and/or an area proximate to the tumor contains the complementary part of the associated pair. As another example of targeted therapy, the nanoparticles may be completely or partially on, associated with, and/or contained in a virus to more specifically target therapy. As one example and without limitation, the nanoparticle may be targeted to a site of a tumor that has or may have a viral association. Examples include, but are not limited to, papillomaviruses, polyoma viruses, Epstein-Barr virus (EBV), human herpes virus 8 (HHV-8), hepatitis B virus, and human T-cell lymphotropic virus-1 (HTLV-1). As another example, the nanoparticle may be targeted to, incorporated in, or otherwise located at a tumor cell, e.g., membrane viral capsids and/or envelopes, using a modified-virus and/or adenoma-associated virus (AAV) either alone or in combination with another therapy, e.g., gene therapy. As another example, the nanoparticle may be completely or partially on, associated with, and/or contained in a tumoricidal virus or a virus rendered tumoricidal to provide additional therapy, e.g., a modified herpes simplex virus selectively targeting malignant cells.

Immunotherapy is broadly defined as therapy to a patient that involves modulating at least some part of the immune system, in whole or in part, and whether the immune system involvement stimulates, modulates, suppresses, ameliorates, enhances, treats, etc. the patient. The immunotherapy thus may encompass either activation of the patient's own immune system or suppression of the patient's own immune system, in whole or, more likely, in part. Immunotherapy is used to treat neoplastic disease, infectious diseases, inflammatory disease, degenerative disease, etc.

Immunotherapy may provide one or more exogenous compounds that may be natural in whole or in part, recombinant in whole or in part, and/or synthetic in whole or in part. The type(s) of compounds may be diverse, e.g., small molecules, biologics, enzymes, hormones, protein or peptide factors, gene modulating agents, etc. Examples include, but are not limited to, antibodies including polyclonal and monoclonal antibodies, growth factors, integrins, interleukins, cytokines, chemokines, interferons, membrane-coupled receptors, receptor agonists, receptor antagonists, oligonucleotides, mRNA silencers, siRNA, steroids, etc. Upon administration to a patient, an immunotherapy compound acts on the patient's own immune system in one or more of the ways previously described, e.g., activation, suppression, enhancement, etc. The exogenous compound(s) may act directly or indirectly to provide an outcome. Thus the compound(s) may have a substantially immediate effect, or may have an attenuated or non-immediate effect.

Exemplary immunotherapy compounds include, but are not limited to, the following: polypeptides comprising MHC I and/or MHC II; glycoproteins; APC protein markers; dendritic cell maturation markers; polymers either with or without an lipid group, acrylic polymers, copolymers of lactic acid and glycolic acid; protein, peptide, small molecule, and/or carbohydrate B cell antigens including toxins; carbohydrate targeting moieties; lipid targeting moieties; vaccines including the breast cancer HER2/neu peptide, cervical cancer HPV vaccine, colorectal cancer vaccine including vaccines against CEA protein, kidney cancer vaccine, lymphoma vaccine, lung cancer vaccine include BLP25 (STIMUVAX®), pancreatic cancer vaccine including GVAX and ipilimumab (YERVOY®), prostate cancer vaccine including prostate-specific antigen (PSA) and prostate-specific membrane antigen (PSMA) and PROSTVAC-VF); Toll-Like Receptor (TLR)-1 to 10, TLR agonist; toxins; biologics including but not limited to the following: the farnesyltransferase inhibitor tipifarnib; farnesyl and geranylgeranyl transferase inhibitors; the multikinase inhibitor sorafenib combined with tipifarnib; and bortezomib and tipifarnib.

Exemplary markers to evaluate therapy include, but are not limited to, the following: alpha-fetoprotein (AFP) for liver and germ cell tumors; beta-2-microglobulin (B2M); beta-human chorionic gonadotropin (beta-hCG); BCR-ABL fusion gene; BRAF mutation V600E; CA15-3/CA27.29 in blood for breast cancer; CA19-9 for pancreatic cancer, gallbladder cancer, bile duct cancer, and gastric cancer; BCA-125 in blood for ovarian cancer; calcitonin in blood for medullary thyroid cancer; carcinoembryonic antigen (CEA) in blood for colorectal and breast cancer; CD20 in blood for non-Hodgkin lymphoma; chromogranin A (CgA) in blood for neuroendocrine tumors; chromosomes 3, 7, 17, and 9p21 in urine for bladder cancer; cytokeratin fragments 21-1 in blood for lung cancer; EGFR mutation analysis in tumors (estrogen receptor (ER)/progesterone receptor (PR)) for non-small cell lung cancer and breast cancer; fibrin/fibrinogen in urine for bladder cancer; HE4 in blood for ovarian cancer; HER2/neu in tumor immunoglobulins for breast, gastric, and esophageal cancer, and in blood and urine for multiple myeloma and Waldenstrom macroglobulinemia; KIT in tumors for gastrointestinal stromal tumor and mucosal melanoma; KRAS mutation analysis in tumor for colorectal and non-small cell lung cancer; lactate dehydrogenase in blood for germ cell tumors; nuclear matrix protein 22 in urine for bladder cancer; prostate-specific antigen (PSA) in blood for prostate cancer; thyroglobulin in tumor for thyroid cancer; urokinase plasminogen activator (uPA) and plasminogen activator inhibitor (PAI-1) in tumor for breast cancer; 5-protein signature (Ova1) in blood for ovarian cancer; 21-gene signature (Oncotype DX) in tumor to evaluate risk of recurrence in breast cancer; 70-gene signature (Mammaprint) in tumor for breast cancer. Generally, a decrease from a patient's previous value and/or a normal level and/or a normal baseline level for the particular individual indicates therapy efficacy and/or decreased tumor burden.

The effect of any exogenous immunotherapy compound may depend upon its method of delivery which, in turn, may determine how rapidly the compound is present at the site of action (sometimes termed target site). The target site may be one or more types of leukocytes that are classically regarded as involved with cell-mediated immunity, i.e., lymphocytes, e.g., T-lymphocytes, B-lymphocytes, or other cell types such as macrophages, natural killer cells, mast cells, basophils, dendritic cells, etc. It will be appreciated that many if not all of these cell types may contain genetic modifications to affect their normal physiological function in the immunologic process. For example and without limitation, genetically modified enhancement, decrease, attenuation, facilitation of various targeting and activation function may be achieved using techniques known in the art. Because of the myriad types of administration routes coupled with the myriad types of exogenous immunotherapy compounds, delivery may be a consideration in patient therapy. The exogenous compounds may be delivered in a number of ways. One embodiment provides nanoparticle delivery, with nanoparticles described herein and as known in the art, and which include but are not limited to, quantum dots.

Figure 5:
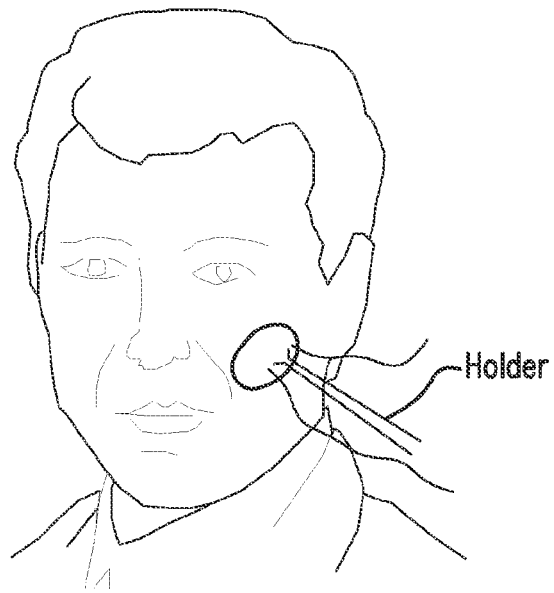
FIG. 5 illustrates one embodiment after placement of the magnet for a facial skin tumor.

As described herein, nanoparticles may be biocompatible or rendered biocompatible. In one embodiment, nanoparticles may be associated with liposomes. Nanoparticles may contain and/or be coated with, in whole or in part, materials such as ferric oxide, carbon, diamond, zinc oxide, gold, etc. providing methods to target the nanoparticles to a particular cellular, physiologic, and/or anatomic site. For example, one embodiment described herein uses an alternating magnet or electromagnetic radiation with a metal-containing nanoparticle (e.g., ferromagnetic nanoparticle) to effect therapy (see, e.g., FIG. 5).

Nanoparticles are a particularly advantageous delivery vehicle for several reasons. Their small nanoscale size permits their entry, localization, and/or accumulation into anatomical and physiological regions otherwise less readily accessible. Their nanoscale size likewise permits intravenous administration, providing systemic access via the circulatory system.

Permutations of any of these embodiments are included in the inventive method. Illustrative but non-limiting examples include polymer-coated nanoparticles, nanoparticle-stabilized liposome-polymer nanocarriers, nanoparticles contained in or formulated with liposomes, micelles, reverse micelles, etc.

As described herein, the nanoparticles contain a targeting agent, such as an antibody, a specific binding pair member, etc., ensuring the nanoparticles administered to a patient are directed to a target site, e.g., a tumor site, a particular cellular receptor, etc. Using this approach ensures the thermotherapy is targeted.

In one embodiment, a cancer patient receives immunosuppressive therapy. Such immunosuppressive therapy may involve chemotherapy, radiation therapy, or both chemotherapy and radiation therapy. Prior to the patient receiving immunotherapy, the patient provides a blood sample from which leukocytes are separated. The leukocytes are then cultured in vitro in an environment to support their growth and maintenance; T cells are treated with the cytokine interleukin-2 (IL-2). The cultured autologous leukocytes, termed lymphokine-activated killer cells (LAK cells), are then re-infused into the patient, providing a bolster to the patient's suppressed immune system. In this embodiment, the combination of hyperthermal therapy with immunotherapy may be used to advantage. This is because the patient receives combination therapy: (i) chemotherapy and/or radiation therapy, which may or may not be finely targeted to a specific malignancy, tumor type, tumor location, etc.; (ii) hyperthermal therapy to destroy cells at increased temperature that does not result in protein denaturation thus sparing normal cells and normal cellular processes, and provided at a specific location to which the therapy is directed at a target site; and (iii) immunotherapy to bolster or restore or augment the patient's own immune response and thus bolster or augment natural immune functions. The combination therapy avoids total immunosuppression and provides the patient at least a modicum of immune function during recovery. The combination therapy permits a decreased dose of nanoparticles administered, decreased frequency of hyperthermal therapy, or both, providing less of a therapy burden to the patient. The combination therapy, because it considers the immune system, facilitates patient recovery or comfort with fewer complications of the immunosuppressive treatment itself.

To effect therapy, one or more large energy generation sources or units can provide a source of thermal energy for a large part of the body. Alternatively, a simpler, e.g., smaller, energy generation source or unit, e.g., a hand-held unit, can provide a source of thermal energy to labeled nanoparticles when brought close to the desired tissue area. In one embodiment, electromagnetic radiation is the energy source, e.g., from ultraviolet radiation up to radiofrequency waves. In one embodiment, ultrasound energy is the energy source, e.g., an ultrasonic unit focusing ultrasound waves to the desired area of the body to heat the nanoparticles. In one embodiment, an alternating magnetic field is used to heat the magnetic nanoparticles and treat the tumor. An alternating magnetic field is readily created, e.g., by a simple iron rod surrounded by a coil of wire with alternating current.

The device providing the energy source can be a magnet, microwave unit, a radiofrequency (RF) probe, an ultrasound probe, etc. The device can be any size. The device may be stationary, hand held, or introduced into the body by invasive or minimally invasive methods, e.g., introduced by a catheter. The device can be brought close, adjacent, or proximate to the target site. If the device is an alternating magnetic field, the oscillation of the magnetic field can range from a few Hz to gigahertz with appropriate magnetic field force according to the distance from the target. In one embodiment, e.g., 0.000001 Tesla to 11 Tesla, with a distance of 0.1 cm to 15 cm, are used.

In one embodiment, non-magnetic, magnetic, or paramagnetic nanoparticles labeled with the tumor antibody and/or fluorescent moieties are used to selectively bind to tumor cells.

In one embodiment, the method is used to effect therapy of a non-malignant tumor. In one embodiment, the method is used on normal cells with a propensity or predisposition to malfunction and/or grow excessively. One such example includes myofibroblasts, which are activated after coronary stent placement. Another such example includes nerve cells, which may be aggravated and thus produce chronic pain. In these cases, a cell specific antibody is combined with nanoparticles and conjugated ACPPs to attach nanoparticles to axons of these nerves. The nerves are then treated non-invasively to achieve a localized temperature up to about 60° C. to effect selective ablation and, thus, to prevent transmission of pain sensations. Another such example uses the method therapeutically to stimulate tissue healing, e.g., a beneficial thermal effect in creating heat shock proteins and encouraging circulation in the area.

In one embodiment, after injecting the nanoparticle composition, either with nanoparticles alone or combined with ACPP, the patient target(s) is exposed to an energy source (electromagnetic radiation energy, ultrasound energy, an alternating magnetic field, etc. as previously described) to increase the temperature of the cells that are complexed with, i.e., that contain, the nanoparticles. In one embodiment, selection of a desired temperature, e.g., 39° C. to 58° C., duration, and/or imaging means as subsequently described, selectively damages the tumor cells while protecting the normal cells. With surgical tumor excision, the tumor margins, which contain nanoparticles, are visualized by imaging means, e.g., photoacoustic imaging, magnetic resonance imaging, thermal imaging, etc. A magnetic resonance imaging unit can be used for imaging, alone, or for thermal imaging of the tissue. Alternatively, photoacoustic sound can be modified, e.g., amplified, so the sound can be heard by the surgeon during therapy and be used as a diagnostic test for the presence of the remaining tumor cells in the surrounding unexcised tissue, guiding further treatment.

The method also permits remote treatment of a patient in need of such treatment but unable to travel for on-site treatment by electronic communication, e.g., Internet communication. The communication means is operatively linked to software that controls an energy source and an imaging system. The system is integrated to provide an energy source as previously described, e.g., ultrasound, electromagnetic radiation, alternating magnetic field, and a thermal imaging system as previously described, e.g., photoacoustic or MRI. Using this embodiment, medical personnel provide instructions that control both the imaging device and the heating device. When a desired temperature in the target tissue is achieved, the software modifies the thermal energy output, e.g., it maintains the tissue temperature at the desired thermal energy level or it increases or decreases the thermal energy at its source. In one embodiment, the system is equipped with a tracking device and pattern recognition software to maintain an accurate location of the treatment site. In one embodiment, any variation, such as patient movement or a change in settings, triggers a failsafe system to terminate the procedure. In one embodiment, the entire system provides real-time results to medical personnel at a location remote from the patient (e.g., down the hall or in a different country), and these medical personnel can control the entire process electronically by Internet connection. The information is software controlled, medical personnel regulated, and subject to the above-described failsafe mechanisms and privacy standards as needed.

The target site is heated to the desired temperature to hyperthermally treat the target site using standard heating instruments and equipment for heating tissue and standard equipment for visualizing the dye in the target site that has been released from the heat sensitive particles. For example, the heating equipment preferably includes suitable heat or energy source that is able to focus the heat or energy on the target and is able to control heat and temperature of the tissue. The heat source can be an electrical resistance heating element, or an indirectly heated element. The heating device can also have a radiation energy source for producing heat at the target site, such as a radio frequency (RF) device, ultrasonic generators, laser, or infrared device. One example of an RF generator device for hyperthermally treating tissue in a selected target site is disclosed in U.S. Pat. No. 6,197,022, which is hereby incorporated by reference in its entirety. Examples of suitable ultrasonic devices for delivering ultrasonic hyperthermia are disclosed in U.S. Pat. Nos. 4,620,546, 4,658,828 and 4,586,512, the disclosures of which are hereby incorporated by reference in their entirety.

In one embodiment, the duration of the applied radiation energy may be from about a femtosecond to about 15 minutes. In one embodiment, the duration of the applied radiation energy may be from about one picosecond to about 15 minutes. In one embodiment, the duration of the applied radiation energy may be from about one nanosecond to about 15 minutes. In one embodiment, the duration of the applied radiation energy may be from about one microsecond to about 15 minutes. In one embodiment, the duration of the applied radiation energy may be from about 1 second to about 15 minutes. In one embodiment, the duration of the applied radiation energy may be from about 1 second to about 15 seconds.

In one embodiment, the temperature at which the radiation energy is applied ranges between about 45° C. to about 49° C. In one embodiment, the temperature at which the radiation energy is applied ranges between about 39° C. to about 58° C. In one embodiment, the temperature at which the radiation energy is applied ranges between about 39° C. to about 45° C. In one embodiment, the temperature at which the radiation energy is applied ranges between about 45° C. to about 49° C. In one embodiment, the temperature at which the radiation energy is applied ranges between about 49° C. to about 56° C. For example and without limitation, relatively brief treatment times are used for circulating cells (e.g., cells in vessels of the circulatory and lymphatic systems). Relatively longer laser pulses may also be used for tissues located deep inside the body. In one embodiment, the ultrasound frequency can range between 0.5 KHz to 200 MHz. In one embodiment, the ultrasound frequency can range between 0.5 MHz to 10 MHz. In one embodiment, the ultrasound frequency can range between 10 MHz to 30 MHz. In one embodiment, the ultrasound frequency can range between 5 MHz to 80 MHz.

In one embodiment, the heat source includes a probe having a tip with the heating element or energy emitting element attached thereto. The energy emitting element can be an optical fiber operatively connected to a laser, infrared or ultraviolet light source. The probe preferably includes a suitable control mechanism for manipulating the probe to the target site and a control for controlling the energy applied to the target site. In one embodiment the wavelength of light is selected to be in the range between 350 nm to 1300 nm. In another embodiment the wavelength of light is selected to be in the range between 450 nm to 600 nm.

A suitable device for hyperthermally treating the tissue in a target site is shown in the figure. The device 10 includes a probe 12 having an optical fiber 14 with a distal end 16 for emitting a laser light to heat the tissue 17. Preferably, the end 16 of optical fiber 14 can focus the light source on the target site 17. Optical fiber 14 is connected to laser generator 18 that is able to generate a laser beam of sufficient intensity and within wavelength for hyperthermally treating tissue. For use of the method in making a diagnostic assessment or for therapy, the tissue is treated to a temperature of at least 41° C. to 56° C., and preferably at least 42° C. to 56° C. In a preferred embodiment, probe 12 includes a second optical fiber 20 having a distal end 22 and a third optical fiber 24 having a distal end 26. Optical fiber 20 is operatively connected to a light source 28, such as a laser, that is able to emit a light beam having a wavelength capable of fluorescing a fluorescent dye in the target area when the dye is released from the heat sensitive particles. Optical fiber 24 is operatively connected to a suitable imaging device 30 for capturing the fluoresced light from the excited dye and visualizing and producing an image of the fluorescing dye in the target site. Imaging device 30 can be a CCD or a device equivalent to a funduscope. An example of a suitable funduscope is disclosed in U.S. Pat. No. 4,891,043 to Zeimer, which is hereby incorporated by reference in its entirety.

In another embodiment of the invention, the probe can include a heating element or a device for receiving a heated fluid that can transfer the heat to the tissue in the target site. The probe can include an expandable bladder member for receiving a heated fluid delivered from a fluid-heating source. In still another embodiment, the expandable bladder includes a permeable portion so that the heated fluid can be applied directly to the target site. A suitable aspirating device is preferably included to remove the excess heating fluid when applied directly to the target site.

In one embodiment, the target site is the retina or choroid in the eye of the patient. The heating and visualizing instrument includes a laser capable of focusing a laser beam on the target site where the laser beam has a wavelength and intensity to heat the cells to a temperature of at least 42° C. In one embodiment, the laser heats the cells to a temperature of 50° C. or below and preferably to about 42° C. to 56° C. The instrument also includes or is used in combination with a funduscope to excite or fluoresce the dye that has been released in the target site to capture and visualize the fluorescing dye. A funduscope that can be used is disclosed in U.S. Pat. No. 6,248,727, which is hereby incorporated by reference in its entirety. The laser source is selected to provide sufficient energy to heat the tissue in the target site to the desired temperature.

The fluorescent dye is encapsulated in a suitable heat sensitive particle and introduced into the patient in a location to be visualized in the target site. The heat sensitive particles can be microcapsules, or nanocapsules that are able to release the dye at a temperature of about 41° C., and preferably 42° C. or higher. In preferred embodiments, the fluorescent dyes are incorporated into heat sensitive liposomes that have a phase transition temperature at the temperature of hyperthermia. In one embodiment, the liposomes have a phase transition temperature within the desired temperature range that tissue or cells are to be heated.

In one embodiment, the liposomes have a phase transition temperature of at least 41° C. and preferably at least 42° C. In a preferred embodiment, the liposomes have a phase transition temperature of about 45° C. to about 50° C.

The liposomes can be made by various processes as known in the art. The phase transition temperature of the phospholipid is selected to control the temperature that the dye and other components are released from the liposomes. Phospholipids are known to have different phase transition temperatures and can be used to produce liposomes having release temperatures corresponding to the phase transition of the phospholipids. Suitable phospholipids include, for example, dimyristoylphosphatidyl choline having a phase transition temperature of 23.9° C., palmitoylmyristoylphosphatidyl choline having a phase transition temperature of 27.2° C., myristolypalmitoylphosphatidyl choline having a phase transition temperature of 35.3° C., dipalmitoylphosphatidyl choline having a phase transition temperature of 41.4° C., stearoylpalmitoylphosphatidyl choline having a phase transition temperature of 44.0° C., palmitoylstearolyphosphatidyl choline having a phase transition of 47.4° C., and distearolyphosphatidyl choline having a phase transition temperature of 54.9° C. Another suitable phospholipid is a synthetic $C_{17}$ phosphatidyl choline from Aventi Inc. having a phase transition temperature of about 48° C.-49° C.

The phase transition temperature and the release temperature of the liposomes can be selected by combining the different phospholipids during the production of the liposomes according to the respective phase transition temperature. The phase transition of the resulting liposome membrane is generally proportional to the ratio by weight of the individual phospholipids. Thus, the composition of the phospholipids are selected based on the respective phase transition temperature so that the phase transition temperature of the liposome membrane will fall within the selected range. By adjusting the phase transition temperature of the liposome membrane to the selected range, the temperature at which the liposomes release the dyes and other components can be controlled during hyperthermia.

The liposomes in one embodiment of the invention are preferably prepared so that the liposome membrane has a phase transition temperature of at least 42° C., and preferably about 42° C. to about 50° C. In a preferred embodiment, the liposomes leak or rupture at a temperature of about 49° C. or less, and typically between about 45° C. and 49° C. In one embodiment, the phospholipids have saturated acyl groups. For example, glycerophospholipids can be used that have two acyl groups having 8 or more carbon atoms and where at least one of the acyl groups have at least 10 carbon atoms and typically 12-18 carbon atoms. Examples of suitable phospholipids include hydrogenated lecithin from plants and animals, such as egg yolk lecithin and soybean lecithin. The phospholipid can also be phosphatidyl choline produced from partial or complete synthesis containing mixed acyl groups of lauryl, myristoyl, palmitoyl and stearoyl.

The liposomes can be prepared from a mixture of dipalmitoylphosphatidyl choline and disteroylphosphatidyl choline in a weight ratio of 95:5 to about 5:95 and generally about 80:20 to 20:80. In one embodiment, the liposomes are made from a mixture of dipalmitoylphosphatidyl choline and disteroylphosphatidyl choline in a ratio of 45:55 to about 55:45 provide a phase transition temperature of about 46° C. to about 49° C.

The liposomes of the invention can be prepared by standard processes as known in the art. The liposomes can be unilamellar or multilamellar and have a particle suitable for delivering the dye to the target site. In one embodiment, the liposomes have a particle size of a sufficiently small size to be introduced into the bloodstream of the patient in a location near the target site to flow through the target site.

The liposomes can contain a suitable osmotic pressure controlling agent that is physiologically acceptable to the patient. Examples include sodium chloride, sugars such as glucose, mannitol and sorbitol, and amino acids such as glycine, aspartic acid and glutamic acid. Examples of suitable process for preparing liposomes are disclosed in U.S. Pat. No. 4,235,871 to Papahadjopoulos et al. and U.S. Pat. No. 4,522,803 to Lenk, which are hereby incorporated by reference in their entirety.

The liposomes of the invention contain a dye that is able to fluoresce and that can be visualized in the target site by exciting with a light source that is amenable to the target site and the patient. The fluorescent dye can be any fluorescent that is suitable for encapsulation and is physiologically compatible. Preferably, the fluorescent dye is quenched when encapsulated at an appropriate concentration. The quenching concentration is a sufficiently high concentration to mask or minimize detection of fluorescence when illuminated by a fluorescing light source. The quenching concentration can be determined by routine experimentation as known in the art. When heated, the heat sensitive liposomes rupture or leak the dye and other components of the liposome so that the dye is diluted in the target site to a suitable concentration where the dye can be fluoresced and visualized upon excitation by a suitable light source. Examples of suitable dyes include 6-carboxyfluorescein and its derivatives. Suitable fluorescent dyes can be excited by an emit light at wavelengths that are not strongly absorbed by the tissue. Other suitable dyes include indocyanin green and aluminum phthalocyaninetetrasulfonate. It will be understood that the fluorescing light source and the visualizing instrument are selected according to the wavelength of the fluorescing dye to visualize the dye.

In one embodiment, the dye is selected to fluoresce in the presence of a light from an argon laser, a helium-neon laser or infrared laser. Preferably the dye is selected to be compatible with the exciting light or laser source to fluoresce when subjected to the light or laser beam. A suitable dye is sold under the tradename D-275 by Molecular Probes, Inc. and fluoresces green when exposed to light from an argon laser at 484 nm. A dye sold under the tradename D-1121 fluoresces orange when exposed to a long wavelength laser light at 560-574 nm. One preferred dye is an infrared excitable dye $Dilc_{18}(7)$, which fluoresces at a wavelength of 740-780 nm.

In one embodiment of the invention, a fluorescent dye is encapsulated in liposomes having a phase transition temperature of 42° C. to 50° C., and preferably about 45° C. to 49° C. In another embodiment, the liposomes have a phase transition temperature to release the dye at a temperature of about 46° C. to about 49° C. The liposomes are injected into the bloodstream of the patient in a location where the liposomes flow to the target site. In some embodiments, the liposomes can be introduced directly to the target site intravenously, subcutaneously or topically. A hyperthermal heat source and a dye exciting light source are applied to the target site. The hyperthermal heat source, which is preferably a laser light beam, is focused on the target site to heat the tissue and the cells to a temperature of at least 42° C. to hyperthermally treat the tissue and kill the cells. The hyperthermal heat source also heats the liposomes to a temperature at least equal to the phase transition temperature to release the dye. The fluorescing light source excites the dye so that the fluorescing dye in the target site can be detected and visualized. By encapsulating the fluorescent dye in liposomes having a phase transition of at least 42° C., the detection of the fluorescing dye provides a positive indication to the operator that the desired tissue temperature has been obtained that is necessary to hyperthermally treat the tissue. The phase transition temperature of the liposomes is selected according to desired minimum temperature that the tissue is to be heated. The hyperthermia energy source is applied to the target site for a time sufficient to treat the tissue to the desired level. Generally, the tissue is heated to a temperature of at least 42° C. for 1-15 minutes and preferably 1-10 minutes.

In one preferred embodiment of the invention, the liposomes contain a suitable drug or photosensitizing agent. The drugs preferably show a synergistic effect when combined with the hyperthermia treatment of the invention. The release of the drugs from the liposomes provide an improved targeting effect by releasing the drugs by the heat source in the target site. Suitable drugs include antitumor agents such as cisplatin, carboplatin, tetraplatin and iproplatin. Suitable anticancer drugs include adriamycin, mitomycin C, actinomycin, ansamitocin and its derivatives, bleomycin, Ara-C, daunomycin, metabolic antagonists such as 5-FU, methotrexate, isobutyl 5-fluoro-6-E-furfurylideneamino-xy-1,2,3,4,5,6 hexahydro-2,4-dioxopyrimidine-5-carboxylate. Other antitumor agents include melpharan, mitoxantrone and lymphokines. Antitumor therapy involving biologics, e.g., DNA, RNA, protein, siRNA, genes or portions thereof, etc., may be administered.

The amount of the particular drug entrapped in the liposomes are selected according to the desired therapeutic dose and the unit dose.

In one embodiment, the method administers a drug or drugs and/or a radiotracer, either liposome-contained or not, contained in nanoparticles. The nanoparticles are formulated, using methods known by one skilled in the art, to release the drug and/or radiotracer when a certain temperature is attained. As only one example, the nanoparticles can be conjugated with thermosensitive polymers that will disassociate and hence will release the drug and/or radiotracer upon reaching and exceeding a given temperature.

Such thermosensitive polymers and methods of formulating these thermosensitive polymers with or in nanoparticles containing chemotherapy drugs and/or a radiotracer are known in the art. Embodiments of the disclosed method use combinations of thermosensitive polymers with, e.g., known pH sensitive polymers, magnetically controlled release agents, magnetoliposome agents, thermosensitive liposomes entrapping iron oxide nanoparticles, etc., to achieve controlled drug release. The following non-limited examples are expressly incorporated by reference herein and generally describe such polymers and methods. Alavarez-Lorenzo et al. describe temperature-sensitive chitosan-poly(N-isopropylacrylamide) interpenetrated networks that have enhanced loading capacity and controlled release properties. Alexander et al. describe variable architecture polymers that are temperature- and pH-responsive, termed smart polymers, including synthetic copolymers and polymer derivatives. Hoare et al. describe nanoparticles encased in poly(N-isopropylacrylamide) (PNIPAM) that are heated by magnetic induction. Mornet et al. disclose poloxamers and poloxamines that are suitable vehicles acid (PMA) polymers that are modified with thiol groups ($PMA_{SH}$) and are suitable vehicles for delivery of the nanoparticles and anticancer drug(s). In one embodiment, the nanoparticles are conjugated with radiological imaging compounds, e.g., gadolinium used in magnetic resonance imaging. In one embodiment, the nanoparticles are conjugated with metabolically active compounds, e.g., F-18FDG used to visualize tumors and metastatic lesions using positron emission tomography-computed tomography (PET-CT) scanning. It is known that heating cells to a temperature greater than 60° C. denatures its proteins and/or coagulates its contents, but due to the specificity of the antibody targeting, only the tumor cells are thermally treated; normal cells are unperturbed. Thus, these methods are used either singly or in combination to achieve desired effects of targeting tumor cells, and specifically tumor stem cells that are otherwise resistant to treatment and/or that elude detection.

The specific tissue site to be thermally treated, containing the complex of polymer-coated drug-containing nanoparticle and antibody complex, is thermally treated by any appropriate modality (e.g., electromagnetic radiation, ultrasonic radiation, alternating magnetic field, etc.) to a first temperature at which the polymer and/or liposome releases drug. In one embodiment, this temperature is achieved relatively early in thermal treatment, e.g., from 37° C. to 43° C. After release, the nanoparticles are further thermally treated to achieve or exceed a second temperature, e.g., from 43° C. to 45° C., 43° C. to 58° C., 45° C. to 50° C., 50° C. to 58° C., 58° C. to 60° C., to greater than 58° C., or to greater than 60° C. Without being bound by a single theory, the first thermal treatment primes the tumor cells and the tumor stem cells. When the patient is receiving or has received chemotherapy, the priming results in the tumor cells' enhanced susceptibility to both the effect of chemotherapeutic drug and the damage from the rise of thermal energy inside the tumor mass. When the patient is receiving thermal therapy singly, or before chemotherapy, the priming results in the tumor cells' enhanced susceptibility to the damage from the rise of thermal energy inside the tumor mass, then are further damaged upon administration of high doses of chemotherapy, either locally administered to target to the tumor site. At the relatively high temperatures at or exceeding 43° C., thermal damage is relatively selective in that it occurs primarily to cells with higher metabolisms, i.e., tumor cells. The method thus leaves non-tumor cells unperturbed or minimally perturbed by the treatment.

Examples of suitable photosensitive (photosensitizer) agents include aminolevulinic acid, porphyrin derivatives, porpurine derivatives, NPE-6, ATX-10, plant derived photosensitizers. Other synthetic sensitizers such as $SNET_2$ and Lutex can be used. Preferably, the photosensitizers are used in non-toxic amounts. In other embodiments, the liposome compositions can contain liposomes that encapsulate a hyperthermic potentiating agent such as perfluorooctyliodide, perfluorotributylamine, perfluorotripropylamine, and perfluorooctylbromide. Examples of liposome encapsulated potentiators are disclosed in U.S. Pat. No. 5,149,319 to Unger, which is hereby incorporated by reference in its entirety. Other bioactive agents that can be delivered to the target site by encapsulating in liposomes include anti-inflammatory agents, antibiotics, antibacterial agents, antifungal agents, anti-neoplastic agents and antiparasitic agents. Examples of anti-neoplastic agents include aclacinomycins, chromycins and olivomycins.

In another embodiment of the invention, the liposome composition contains a mixture of liposomes having different phase transition temperature to release the components at different temperatures. In one embodiment, the liposome composition contains liposomes encapsulating a first dye and having a phase transition temperature of 42° C. to about 45° C. and liposomes encapsulating a second dye and having a phase transition temperature of about 50° C. or higher. In one embodiment, the second dye is encapsulated in liposome that release the dye at a temperature range of 50° C. to 60° C. Preferably, the second dye is able to fluoresce at different color than the first dye so that the dyes are distinguishable. In this embodiment, the liposome composition is delivered to the target and the target site is subjected to hyperthermia temperatures. As the tissue in the target site is heated to at least 42° C., the first liposomes rupture or release the first dye so that the first dye is visualized and detected in the target site. The detection of the first dye in the target site enables the operator to monitor the temperature of the tissue in the target site and to indicate that a hyperthermal temperature has been attained in the tissue at the target site. During hyperthermia, it is difficult to determine and monitor the actual temperature of the tissue and care must be taken to avoid overheating of the tissue and denaturization of the proteins. In preferred embodiments of the invention, the hyperthermal treatment does not exceed the protein denaturization temperature. In this embodiment, the second liposomes are selected to rupture or release the second dye at or slightly below the protein denaturization temperature. In this manner, the second dye is released and visualized to provide the operator with an indication that the tissue is heated to the protein denaturization temperature. The heat source is then adjusted by the operator to reduce the energy applied to the target site to avoid protein denaturization.

In another embodiment, the liposome composition can contain several liposomes that can leak or rupture at different temperatures to release the dyes at incremental temperatures as the temperature of the target site increases. In one embodiment, the liposomes can be selected to leak or rupture the dye at 2° C. intervals between about 42° C. and 50° C. The dyes for each liposome can be different to fluoresce a different color so that the different colors indicate a different temperature of the target site. In other embodiments of the invention, the tissue in the target site can be irradiated by beta radiation from strontium or iridium isotopes. Gamma radiation from $P^{32}$, iodine-95, and palladium-90 can also be used. The radioactive isotopes can be delivered as small particles to the target site in combination with the hyperthermia treatment.

In another embodiment, the method combines thermal therapy, either with or without chemotherapy, with localized internal ionizing radiation therapy to treat a patient in need of such treatment. The conditions of thermal therapy are described herein, and chemotherapy is also described herein and is known by those skilled in this art. The addition of localized internal ionization radiation therapy damage or destroy the endothelial cells lining the vessels proximate the tumor site, in effect starving the tumor of its nutrient supply source. This embodiment of the method administers a composition of targeted nanoparticles that containing an anti-tumor antibody, a radioactive isotope, and may also contain drug, to a patient. The patient receives an internal dose of radiation from the administered radioactive nanoparticles, i.e., internal radiation therapy, in contrast to external radiation therapy where the patient receives radiation from an external radiation source. This combination of localized thermotherapy and localized internal radiation therapy, and optionally localized chemotherapy, i.e., drug therapy, increases the likelihood of eradicating both existing tumor cells and tumor cell progenitors, as well as damaging endothelial cells in adjacent tumor-associated vessels. The method thus results in more robust therapy and increased chances of patient survival.

This embodiment relies on thermotherapy provided at the target site, and internal radiation therapy at the target site. In general, and as subsequently described, a composition of anti-tumor cell antibody associated with radioactive nanoparticles is administered to the patient, e.g., by intravenous injection. The tumor cell specificity of the antibody localizes the composition at the tumor site for thermotherapy, i.e., controlled hyperthermal therapy, and the associated radioactive nanoparticles damage or destroy the vessels adjacent the tumor, e.g., blood vessels, lymphatic vessels.

Thermotherapy is administered under conditions sufficient to result in targeted therapy to cells in the patient, as described herein. Radiation therapy results in damage to the tumor cells and adjacent endothelial cells in vessels providing blood, lymph, etc. to the tumor, i.e., to vessels feeding the tumor. As one example, nanoparticles can be coated with antitumor antibody to target, e.g., glioma cells in a patient with a brain tumor; an antibacterial antibody and an appropriate antibiotic, etc. Nanoparticles may be conjugated either directly with radioisotopes, or radioisotopes may be conjuaged with polymers that are subsequently used coat the nanoparticles. Monoclonal antibodies may be used to attach coated nanoparticles to tumor cell surface markers, bacterial cell surface markers, etc. Nanoparticles are then provided, e.g., intravenously injected using a needle or catheter, applied through an external orifice, to target the desired location. The dose can vary, e.g., from 10 µCi to 20,000 µCi. Radioisotopes producing α radiation are preferred, examples of which are $At^{211}$ (α particle, duration 7.2 hr, penetration 0.08); $Ac^{225}$ (α, β particle, duration 10 days, penetration 10 0.1 mm); $Bi^{212}$ (α, β particle, duration 60.6 min, penetration 0.09); $Bi^{213}$ (α, β particle, duration 46 min, penetration >0.1 mm); $Ra^{223}$ (α, β particle, duration 11.4 days, penetration >0.1 mm); $Pb^{212}$ (α, β particle, duration 10.6 hr, penetration >0.1 mm); $Tb^{149}$ (α, β particle, duration 4.2 hr, penetration >0.1 mm); $I^{131}$ (α, λ particle, duration 193 hr, penetration 2.0 mm); $Cu^{64}$ (α, λ particle, duration 193 hr, penetration 2.0 mm); $I^{131}$ (α, λ particle, duration 193 hr, penetration 2.0 mm); and numerous other α emitters that can be similarly used, e.g., $Bi^{213}$, $Bi^{212}$, the boron neutron capture therapy (BNCT) that can be used for superficial radiation penetration of tumor cells or adjacent cells to a depth of 7 µm. Similarly, groups of non-magenetic, paramagnetic, or magnetic nanoparticles can be produced. Polymeric coating of these nanoparticles renders them less toxic to normal tissue. $Iodine^{131}$ may be crosslinked with antibody-coated nanoparticles to label the tumor or bacterial cells, both for therapy and imaging. Anti-integrins or anti-VEGFs may also be incorporated. The nanoparticles may be used simultaneously for drug delivery purposes against these tumor or bacterial cells, with the drug in PDA, PGLA, dextran, dendrimers, PEG, etc. The nanoparticles may be quantum dots, polymer based nanoparticles, colloidal gold nanoparticles, iron oxide nanoparticles, etc. The nanoparticle size may range from 2 nm to 400 nm in one embodiment, and from 5 nm to 200 nm in another embodiment.

Alpha-emitting isotopes emit radiation for a relatively short time, thus their effect will be short lasting and not damage normal tissue adjacent to a tumor. Isotopes of α radiation emitted penetrate the tissue for a relatively short distance. Because the nanoparticles are attracted to the tumor cell membranes, radiation affects not only the tumor cell but also the adjacent faxcular endothelial cells. The endothelial cells are specifically very sensitive to the radiation, therefore their obliteration deprives the tumor cells of their nutrient source.

This treatment combination disrupts the vessels, to narrow the vessel lumen and/or damage the vessels themselves, killing both the tumor cells by the controlled thermotherapy with optional chemotherapy, and disrupting the nutrient source for the tumor and progenitor stem cells.

In one use of this embodiment of combined thermotherapy and radiotherapy, vessels are effected such that the neovascularization in wet age related macular degeneration (wet AMD) is treated. To treat AMD, local choroidal injection is used. The dose can vary depending on the mode of administration, body mass, body size, location of the tumor, etc. A does may range from 10 µCi to 20,000 µCi.

The radioactive nanoparticles for localized internal radiation therapy may be ferromagnetic or nonferromagnetic, as described herein. They may be coated and/or otherwise conjugated, as described herein, with one or more anti-tumor cell antibodies, as described herein, then intravenously injected into or otherwise administered to the patient. The antibody conjugated and/or coated radioactive nanoparticles then selectively bind to the targeted tumor cells, with the nanoparticles emitting either alpha radiation, gamma radiation, or beta radiation within a localized diameter of 1 mm to 2 mm from the site. The 1 mm to 2 mm radiation penetration range self-limits the radiation effect to the tumor-localized site, while desirably damaging endothelial cells adjacent the tumor. The radiation range damages endothelial cells in vessels feeding the tumor, diminishing or obliterating its nutrient source and in effect starving the tumor cells, as well as damaging tumor progenitor cells. The method targets all sites of tumor cells, and therefore treats both the primary lesion site and any metastatic sites.

Thermotherapy in combination with radiotherapy is performed using a controlled energy source, e.g., computer controlled, as described herein. A local magnetic and/or electromagnetic field is applied and monitored as described herein, e.g., MRI or photoacoustic imaging. In this way, the targeted cells and associated and proximate vasculature are affected. Non-targeted cells and distal vasculature, i.e., more than 1 mm to 2 mm from the tumor localized site, are not affected.

Another embodiment of the invention images the heat (temperature) production inside the eye (target) tissue. The desired temperature is achieved using a laser and photoacoustic imaging technique.

It is known that light can generate sound waves. This is the basis of photoacoustic technology. Some of the delivered energy, e.g., by laser, will be absorbed and converted into heat, leading to transient thermoelastic expansion and thus ultrasonic emission. The generated ultrasonic waves are then detected by ultrasonic transducers to form images. It is known that optical absorption is closely associated with physiologic properties, such as hemoglobin concentration and oxygen saturation. As a result, the magnitude of the ultrasonic emission, i.e., the photoacoustic signal, that is proportional to the local energy deposition, reveals physiological specific optical absorption contrast. Two- or three-dimensional images of the targeted tissues can then be formed.

A photoacoustic image is independently generated from an ultrasonic image, however, it is only visualized, i.e., imaged, by an ultrasonic receiver. Therefore, photoacoustic imaging and ultrasonic imaging should be performed simultaneously, so that the additional changes in the ultrasonic image, resulting from heat expansion, can be seen. In fact, if the ultrasonic wave and photoacoustic wave are parallel, there is no need for any other visualization system, as is the case is opaque tissue. The changes in the ultrasonic images are, however, dependent on the temperature that is created by an additional electromagnetic radiation, such as light, microwave generator, etc. This may be used when microwaves are used to treat intraocular tumors.

Presently, acoustically coupled resonant optical systems are sensitive enough to detect sound waves and differentiate the sound waves based on the temperature generated inside the target tissue. The pulsed light propagates in the ocular tissue uninterrupted until it meets the retino-choroidal tissue where it is differentially absorbed by the tissue producing a spatial distribution of the sound sources that can be imaged by an array of acoustic sensors. All visible light wavelengths and infrared wavelengths up to 1300 nm pass through the eye easily reaching the retina and choroids thus creating a high contrast between these tissue components. In the eye, most of retinal-choroidal pathology relates to the abnormal vessel formation, located at the junction of the retina and the choroids (new vessels), and most of the intraocular tumors are of retinal or choroidal origin permitting light, specifically infrared light at a wavelength of about 780 nm to about 1300 nm to penetrate these structures. The use of incoherent or partially coherent light permits penetration of a few centimeter and maintains a good spatial resolution for diagnosis or treatment. The ocular tissue, from the cornea to the retina, provide a uniform optical density and index of refraction. This index of refraction changes when the light reaches the retina and choroids. However, the contrast image, in ultrasonic imaging, is related to the density and compressibility of the tissue, not the index of refraction, thus permitting photoacoustic imaging to be used in evaluating functional properties of certain molecules based on different optical absorption of molecules, e.g. in oxymetry differentiating oxygenated and reduced hemoglobin.

The diagnostic application of photoacoustic imaging is based on the absorption of electromagnetic energy by different molecules, producing different changes in temperature, pressure, and density. Therefore, photoacoustic image generation is the result of photothermal effect on the tissue or molecules.

If the laser pulse is short enough, a local acoustic effect is generated that can be imaged by an ultrasonic transducer in 2D or 3D format. Because photoacoustic and ultrasonic imaging can share the same array and receiver, the image produced by them can simultaneously provide information on the thermal and anatomical structure, and location of the tissue in a rapid succession such as real time (video) images.

Nanosecond pulses can be generated from a Nd-YAG or Alexandrite laser. The laser delivery can be done either as a combined transducer-laser head or independently through any optical system such as a slit lamp, a direct or indirect ophthalmoscope, or a fundus camera. These instruments have their independent illuminations permitting simultaneous visualization or imaging of the lesion in the eye using multiple imaging modalities, potentially along the previously described markers such as liposomes. In this case, the ultrasonic images are obtained through an independent transducer.

A contrast agent or a marker (biomarker) can be used to enhance the image or temperature (heat production) in the growing cells, such as choroidal neovascularization or tumor cells. For example, gold nanoparticles or tubes can be injected systemically which has a light absorption around 800 nm wavelength, which corresponds to a laser often used in ophthalmology for retinal coagulation purposes. The contrast generated by the above biomarkers in photoacoustic imaging is proportional to the concentration of the biomarker. The gold nanoparticles may be any shape, e.g., spherical, ellipsoidal, tubular (cylindrical). The gold nanoparticles may be solid or hollow. The size of the gold nanoparticles may range from 2 nm to 700 nm. In one embodiment, the size of the gold nanoparticles ranges from 50 nm to 250 nm.

In one embodiment, the thermal images, generated using photoacoustic imaging, can indicate progressively increasing tissue temperature while the area is being treated. In one embodiment, a laser is used to treat the area while photoacoustic imaging is used to generate thermal images of the treatment area. In one embodiment, studies can be conducted to demonstrate the relationship between the photoacoustic images generated, as a result of a certain energy input, and incremental temperature rise in the tissue to create a target temperature, for example, up to 55° C., or any other temperature below the temperature of protein denaturation.

Upon injection of labeled gold nanoparticles, their concentration in the peripheral blood increases. The concentration is reduced within about 24 hours, depending in part on whether the gold nanoparticles contain (poly)ethylene glycol (PEG) groups or not (i.e., are PEGylated or not), because of hepatic clearance. The labeled gold nanoparticles are primarily either present in a bound form, e.g., an antibody-labeled-nanoparticle-cell (malignant cell) complex, or are absorbed by the tumor cells and hence are internalized. Hence, their decreased concentration in peripheral blood (e.g., blood sample obtained by venipuncture) indicates presence of a tumor cell, and provides quantitative information about the number of labeled cells per ml blood. Subsequently the total number of circulating cells in the total whole blood volume of a patient can be calculated. This permits discovery the presence of malignant cells, the ability to quantify the amount of circulating malignant cells from one lesion or multiple metastatic lesions which have metastasized, and to obtain information on their locations in the body.

Obtaining blood samples over a period of time (hours, days, weeks, etc.) and subsequently measuring the concentration of the labeled particles, indicates an increase or decrease in tumor cell shedding as a result of any therapy such as radiation, chemotherapy, thermotherapy, etc. It is thus of diagnostic usefulness, e.g., to monitor efficacy of therapy in a patient receiving therapy for a tumor. The patient receives an intravenous injection of a defined concentration of labeled gold nanoparticles. The concentration of the labeled nanoparticles in the peripheral blood is determined; this is a base level. Then, at a defined interval (e.g., days, weeks, etc.), as determined by a health professional, another peripheral blood concentration of the labeled nanoparticles is determined as an indicator of labeled nanoparticle clearance from the peripheral blood. The decrease in nanoparticle concentration is determined, and correlated with the previous uptake to determine the presence of a tumor, absence of a tumor, or decreased tumor burden (shedding). To illustrate, e.g., a decrease up to 30% to over 95% in 7 days indicates normal clearance of the labeled nanoparticles, and a decrease up to 99% over 7 days to 14 days indicates internalization of the labeled nanoparticles by a tumor. Any significant detection of nanoparticles beyond this time period indicates presence of circulating tumor cells; confirmation is obtained by evaluating a peripheral blood sample obtained by venipuncture and/or by tumor cell histological examination.

In embodiments, the gold nanoparticles can be injected into a tumor, injected into a body cavity, applied over a mucosal surface, and/or applied to skin having a tumor. The absorption of the labeled particles can be used to differentiate a benign tumor from a malignant tumor and simultaneously to treat the tumor by the disclosed method of thermotherapy. In malignant tumors, the gold nanoparticles coated with anti-tumor antibody are absorbed by the tumor and remain in the tissue. In benign tumors, the gold nanoparticles coated with anti-tumor antibody may be initially absorbed by the tumor, but will not remain in the tissue and after 1-2 days are eliminated by systemic absorption.

In one embodiment, a method of delivering antibody-coated nanoparticles to a particular locus, or to a pathological site is disclosed. An example of a particular locus is the nervous system to treat a neurological pathology, e.g., a neurodegenerative disease. An example of a particular pathological site is a known tumor site, e.g., a breast tumor. Administration is either directly to or at the site (i.e., direct injection at the site) or indirectly (e.g., by injection into the bloodstream or other fluid surrounding a site, e.g., cerebrospinal fluid, ocular fluid, ventricles of the brain, etc.). Any site is amenable to the inventive method due to antibody directed targeting or localization. For tumor targeting, the method includes but is not limited to a superficial tumor site. Thus, the following examples are possible. The tumor may be located on an internal or external anatomical site, e.g., skin, extremities, breast, head, neck, and the like. The tumor may affect any organ, e.g., liver, kidney, brain, bone, prostate, ovary, tonsil, thymus, spleen, and the like. The tumor may be located in a deep tissue, such as in muscle, subcutaneous fat cells, intestines, tendons, connective tissue, ligaments, intracranial, and the like. The tumor may be located at a site affecting body fluids, e.g., cerebrospinal fluid, ocular cavity, oral cavity, sinus or sinus cavity, lymph nodes, lymphatic vessel; or the site may be a bodily ventricle, e.g., heart ventricle, brain ventricle, and the like; or the site may be a bodily cavity, e.g., bone cavity, uterus, kidney, bladder, pelvis, or the like.

In one embodiment, the antibody-coated nanoparticles are provided directly to the circulatory system, i.e., either injected into the arterial or venous blood vessel, or delivered by a catheter. In this embodiment, the method is used to treat pathological conditions of blood (e.g., erythrocytes, leukocytes, platelets, and/or their progenitor cells), and/or to provide systemic treatment, e.g., metastatic sites.

In one embodiment, the antibody-coated nanoparticles are magnetic, diamagnetic, paramagnetic, and/or ferromagnetic.

In one embodiment, the method of providing antibody-coated nanoparticles to a site, or for systemic delivery, may be combined with immunologically based B-cells or T-cells that are optionally genetically modified. Such B-cells and T-cells may attack localized and/or unlocalized cancer cells or hematological cancers (e.g., leukemias, lymphomas, etc.). In one embodiment, extra-corporal dialysis and/or plasmapheresis may be used in combination with the inventive method of delivering antibody-coated nanoparticles to accomplish removal of excessive tumor protein in order to protect vital organs, e.g., kidney, liver, brain. In one embodiment, one or more of these therapies are employed at lower doses when used in combination with the method of delivering antibody-coated nanoparticles. In one embodiment, the method of delivering antibody-coated nanoparticles may have a synergistic effect with another therapy, e.g., measured by metrics known to a person of ordinary skill in the art.

In other embodiments, nanoparticles of a material other than gold may be used. These include, without limitation, diamond nanoparticles, platinum nanoparticles, combinations of gold, platinum, carbon, and/or diamond nanoparticles. Any of the above nanoparticles may contain at least one hydroxyl group. All such nanoparticles provide the various diagnostic and therapeutic applications as described above for gold nanoparticles. The sizes and shapes are the same as those described for gold nanoparticles. All such nanoparticles may be covalently attached to (poly)ethyleneglycol, i.e., may be PEGylated.

All such nanoparticles create photoacoustic waves when exposed to an external energy source such as light, ultrasound, lasers, radiation, microwave, etc. The temperature of the nanoparticles rises and their molecules expand. Molecular expansion produces an acoustic sound that can be recorded as a photoacoustic wave signal from an in vivo or in vitro environment. These sounds, photoacoustic signals, are received by acoustic wave detectors or sensors, and are recorded and analyzed. Such methods are known in the art and are similar to signals obtained by endogenous chromophores such as hemoglobin. However, because the gold nanoparticles have stronger absorption of the radiation than other chromophores, e.g., 30% to 99% higher, less energy is required to generate an appropriate signal. The signals of each chromophore can also be differentiated from other signals by ultrasonic spectroscopy. Acoustic wave sensors have acoustic wave resonator elements including piezoelectric material (elements), as known by one skilled in the art. This ability to create and record the acoustic signal is useful for treating tumors, monitoring treatment efficacy, and making diagnoses, distinguishing malignant cells from benign cells, etc. in the same way as previously described for optical tissue. For example, the absence of malignant cells does not generate an image in photoacoustic imaging, and generates a different acoustic signature or characteristic in ultrasound spectroscopy. Thus, the method can evaluate the presence or absence of malignant cells in a human patient. An antitumor antibody-labeled nanoparticle, and a temperature indicating substance, in administered to the patient to form an antibody-labeled-nanoparticle-cell complex at the tumor site. Then, the tumor site is exposed to a radiation energy source under conditions sufficient to achieve a temperature of the complex between 41° C. to 56° C. The acoustic sound produced from the nanoparticle at the site is evaluated and correlated with the presence or absence of malignant cells at the target site by photoacoustic imaging and/or ultrasound spectroscopy.

One embodiment using the above-described labeled nanoparticles is a method to differentiate a tumor or lesion containing malignant cells from one containing benign cells. The nanoparticles are coated with a targeting agent, e.g., antibodies other identifiers known to one skilled in the art, such that they target specific cells when intravenously injected or otherwise administered into a patient.

Cells that are labeled or tagged with gold nanoparticles show 30-40% increase in the resultant acoustic signal, compared to the untagged cells if the cells possess pigmentation. However, a sample of blood or other tissue, or a tumor (e.g., from biopsy) may be obtained and then bleached in vitro to rid the cell of pigment, e.g. melanoma cells. The samples are exposed to an external energy source (light, laser, etc) and the resulting photoacoustic wave signals are measured and analyzed using an ultrasonic spectrometer or other comparable device to determine the presence or absence of the malignant cells. The bleaching step is not needed for the majority of the neoplasms to generate photoacoustic signals, e.g., between a normal cell versus one tagged with gold nanoparticles. to be significant. The differences in the optical absorption of, e.g., light energy, permits differentiation, in vivo and in vitro, between normal and metastatic lesions (tumor cells).

In vitro acoustic cell analysis is performed by taking a biological sample from a patient, e.g., a known volume of blood or other body fluid that may contain circulating malignant cells, e.g., cerebrospinal fluid (CNS), lymphatic fluid, etc. To this fluid sample is added a specific antibody-coated gold nanoparticle. Because of the specificity of the antibody to a particular cellular receptor, protein, or other binding target, the gold nanoparticle binds to the specific cells present in the fluid and is detected, quantitated, monitored, etc. In one embodiment, an optional temperature-indicating substance is added for in vitro evaluation of the circulating tumor cells in the absence of nanoparticle injection. This is useful to indicate is metastatic cells are being released, because a positive result can initiate a search for potential metastatic lesions even if they have not progressed to a size so as to be visible by standard means of examination such as computed tomography (CT) or magnetic resonance imaging (MRI). The sensitivity threshold of recognizing a metastatic lesion is greater than about 1 mm diameter tumor, compared to a sensitivity threshold of greater than about 10 mm diameter tumor with standard means of examination. In either embodiment, the fluid is then analyzed by, e.g., an ultrasonic spectrophotometer or another appropriate device, to measure the number of tagged cells in the fluid. This procedure and analysis can also be adapted for use for other types of body sample such as tissue biopsies as known to one skilled in the art.

In one embodiment, a patient-specific antibody to a tumor is prepared. After biopsy, a specific antibody to the malignant cells of the tumor is generated. The antibody is then coated with gold nanoparticles resulting in an antitumor antibody-labeled nanoparticle. In one embodiment, a biphasic antibody that binds a target via its Fab region is prepared. in one embodiment, an antibody that binds a target via its Fc region is prepared. Such procedures are known to one skilled in the art. These antibody-coated nanoparticles are specific for a specific tumor cell present in the patient forming an antitumor antibody-labeled nanoparticle-cell complex. In one embodiment, the complex may contain a compound, e.g., an antivascular endothelial growth factor and/or an antiproliferative agent. In one embodiment, the antibodies may also be labeled with a fluorescent dye.

As known to one skilled in the art, tumor cell membranes contain numerous receptors. In one embodiment, multiple antibodies against individual antigens may be generated from a tissue biopsy sample. Coating various gold nanoparticles with specific antibody against the tumor cell permits treating a single tumor cells with multiple gold nanoparticles, either alone or with conventional chemotherapy and/or radiation therapy, thus enhancing the tumor-destroying potential of the method. In one embodiment, the combination of targeted hyperthermia plus radiation, etc. provides conditions in which lower than typical levels of radiation are needed to destroy tumors, reducing radiation side-effects.

The above in vitro method and analysis can also be used to determine the temperature (energy) needed to kill tagged malignant cells, or other cells of interest, without damaging the surrounding normal cells. This parameter is incorporated in an in vivo procedure to treat specific tumor or circulating malignant cells. For example, a tumor cell lacking pigmentation (e.g., breast cancer cells) may be killed using lower energy levels than a tumor cell having pigmentation (e.g., melanoma cells).

In one embodiment, a collar positionable to fit on or around a patient's neck or extremities, contains a multiple diode laser that emits specific wavelengths of radiation energy to heat the labeled nanoparticles to a temperature sufficient to thermally destroy the tumor cells and they circulate in the area encompassed by the collar. Other devices that can be used outside or implanted in the body as known to one skilled in the art may incorporate the method for treating and/or destroying malignant cells within other compromised areas of the body such as those having tumors. Because the temperature generated inside the cells tagged with gold particles exceeds that of exposed non-tagged normal cells, this method protects normal cells while damaging the malignant cells.

In one embodiment, the energy source is a free electron laser to provide the hyperthermal treatment. As described, the emitted energy from the free electron laser heats the nanoparticle of the described compositions to the desired temperature.

In one embodiment, the method uses magnetic energy to provide the hyperthermal treatment. This embodiment is used for applying hyperthermal treatment to a lesion that is not accessible to application of light energy. Examples of such inaccessible lesions include brain cells, or cells deep inside the body.

In this embodiment, magnetic nanoparticles are used. In one embodiment, ferromagnetic, e.g., iron oxide or quantum dot, nanoparticles are used, either alone or combined with other magnetic materials or paramagnetic materials such as tungsten, cesium, aluminum, lithium, manganese, sodium, platinum, and/or oxygen. Such magnetic nanoparticles are provided to a patient and exposed to an energy source that provides a magnetic field (e.g., coil, wire) that reverses the direction of the field rapidly using alternating current. In one embodiment, the particles are injected locally, e.g., inside a tumor. In one embodiment, the particles are administered intravenously. In one embodiment, the particles are both injected locally and administered intravenously. In one embodiment, the described composition is introduced via an accessible cavity, such as oral, respiratory, or genitourinary, by injection or catheter. The particles heat up and expand, producing detectable acoustic (sound) waves. In one embodiment, the magnetic field ranges from about 0.0001 Tesla (T) to about 13 T. In one embodiment, the magnetic field ranges from about 0.0001 Tesla (T) to about 11 T. The degree of heat produced upon such exposure induce an expansion of the nanoparticles that is recorded by an ultrasonic transducer, as previously described.

In one embodiment, once delivered to the tumor site, or systemically injected or delivered, the particles are treated with an alternating magnetic field and/or electromagnetic radiation to heat or raise the temperature at the site. In one embodiment, the alternating magnetic field is from 0.0001 T to 13 T, or from 0.0001 T to 11 T, and the alternation frequency is from about 1 GHz to a few seconds, e.g., about 10 seconds, about 5 seconds, or about 2 seconds. In one embodiment, a temperature ranging from about 39° C. to 58° C. is achieved. In one embodiment, a temperature ranging from about 39° C. to about 45° C. is achieved. In one embodiment, a temperature ranging from about 42° C. to about 47° C. is achieved. In one embodiment, a temperature ranging from about 47° C. to about 49° C. is achieved. In one embodiment, a temperature from about 50° C. to about 58° C. is achieved. In one embodiment, the treatment is effected such that the increased temperature is maintained for a period of time ranging from about 5 seconds to 30 minutes. In one embodiment, the treatment is effected such that the increased temperature is maintained for a period of time ranging from about 1 minute to about 30 minutes. In one embodiment, longer times of maintenance at the increased temperature are used.

In one embodiment, simultaneous or substantially simultaneous imaging of the site, e.g., tumor, is effected by means known to the person of ordinary skill in the art, e.g., photoacoustic imaging, magnetic resonance imaging, X-ray imaging, optical coherence tomography, ultrasound imaging, fluorescence imaging, positron imaging, surface enhanced Raman spectroscopy (SERS), and the like. In one embodiment, the method of delivering antibody coated nanoparticles to a site is optionally combined with other therapeutic or medical techniques, e.g. a chemotherapy, radiation therapy, anti-vascular endothelial growth-factor therapy, steroid therapy, and the like.

The magnetic particles are attached to an antibody, as previously described, forming ferromagnetic-antitumor antibody-labeled nanoparticles. These particles provide diagnostic and/or therapeutic thermal heating at a biological target or lesion. A temperature indicating substance is also labeled with the antibody of interest, the ferromagnetic particle, or a combination of both.

As one example, a solution or formulation containing the ferromagnetic-antibody labeled nanoparticles is administered by injection to a human or animal patient or by topical application. The antibody, upon binding to its cellular target, forms a ferromagnetic-antibody labeled nanoparticle-cell complex. After a period of time to allow clearance of the unbound ferromagnetic particles from the patient, the patient is placed in a magnetic field. In one embodiment, this clearance time is less than 2 hours. In one embodiment, this clearance time is 2 hours. In one embodiment, this clearance time ranges between 24 hours to 48 hours. In one embodiment, this clearance time is up to 48 hours. In one embodiment, this clearance time is greater than 48 hours.

Clearance can be assessed the determining the presence of circulating nanoparticles in the patient. as follows. A small volume of patient's blood is placed inside a small electric coil (0.0001 T-0.1 T) in vitro. Altering the magnetic field heats the particles and generates photoacoustic images measured by the ultrasonic transducer, which indicates the present of circulating nanoparticles. The pharmacokinetic of these circulating particles can be measured. When the level of circulating nanoparticles are significantly reduced as described previously, e.g., 2 hours-24 hours post injection, the patient is positioned inside an a magnetic resonance imaging (MRI) instrument or any other applicable instrument known to one skilled in the art.

The applied magnetic field heats the nanoparticles, including the sessile or attached particles to the tumor. The procedure is automatically controlled by photoacoustic imaging monitoring, as subsequently described below. The degree of heat production in the particles induces an expansion of the nanoparticles that is recorded by an ultrasonic transducer previously described. The patient is maintained in the magnetic field until a diagnostic or therapeutic temperature of 42° C. to 56° C. is reached. The time to reach this temperature depends upon the energy applied in one session. The session can be repeated as desired. Generally, the exposure time may vary from <1 minute to >10 minutes. The acoustic sound produced from the nanoparticle at the site is evaluated and correlated with the presence or absence of malignant cells at the target site by photoacoustic imaging and/or ultrasound spectroscopy. A photoacoustic image is created by exposing the tissue or site to electromagnetic radiation, e.g. radiation from 190 nm to about 10 µm; or microwave and radiofrequency radiation produced, e.g., using a laser. If the material has magnetic properties, by reversal of the magnetic field, one can heat the tissue or site; one can also use mechanical waves produced by another ultrasound transducer to heat the tissue or site. These mechanisms create thermoelastic expansion of a molecule that generates a wideband (MHz) emission. The time and amplitude of the photoacoustic images provide information regarding the absorption and location of the source, depending on the degree of thermal expansion of the material, etc., as known to one skilled in the art.

In one embodiment, the method uses magnetic energy to provide the hyperthermal treatment. This embodiment is used for applying hyperthermal treatment to a lesion that is not accessible to application of light energy. Examples of such inaccessible lesions include brain cells, or cells deep inside the body.

In this embodiment, magnetic nanoparticles are used. In one embodiment, ferromagnetic, e.g., iron oxide, nanoparticles are used, either alone or combined with other magnetic or paramagnetic materials. In various embodiments, the described nanoparticle, e.g., ferromagnetic nanoparticle, is carbon coated by methods known in the art, making the nanoparticle more biocompatible, e.g., less toxic. Such magnetic nanoparticles are provided to a patient and exposed to an energy source that provides a magnetic field (e.g., coil, wire) that reverses the direction of the field rapidly using alternating current.

The following methods control the energy applied to the nanoparticles, indicating when to treat after injection of the nanoparticles. A noncoagulative laser or radiofrequency or an acoustic wave, when absorbed, can produce a photoacoustic ultrasonic emission of about 1 MHz or more (two- or three-dimensional), creating an image of a tissue, site, etc. The image, in the form of a graph, curve, etc., shows an amplitude that depends on the amount of thermal energy absorbed or produced at the tissue or site. One can record this temperature increase as an image, regardless of the exact degree increase. This characteristic can be used to distinguish low and high energy applied, e.g. internally generated, by magnetic resonance on the ferromagnetic particles, and can be used to modify the amount of energy required. A computer processor (digital signal processor) can transmit the desired signal from the ultrasound unit to a device, e.g., a laser, radiofrequency device, magnet, etc., as known to one skilled in the art, to increase or decrease the applied energy to achieve potentially any desired temperature for any given situation and site. This energy varies; relatively low heat up to 55° C. for non-coagulative laser treatment, to >60° C. for coagulative laser treatment, to >100° C. in one embodiment and >500° C. in one embodiment for photoablative laser treatment, i.e., very short pulses but very high energy, depending on how deep the target tissue is located inside the body, and the property of the energy absorber inside that targeted tissue. This method results in a treatment that is visible, adjustable, and automatic depending on the needed temperature regardless of the depth of the lesion inside the body. Previously only a light source with an external photographic device could indicate the surface temperature. However these devices and wavelengths are limited by their wavelength, tissue penetration, and tissue water content, limiting light transmission to a few millimeters.

Photoacoustic spectroscopy is very sensitive if a tissue contains any gas. Because animal tissue always contains gases as oxygen, nitrogen, and/or carbon dioxide, any degree of temperature increase causes expansion of these gases at that location. The sensitivity of photoacoustic spectroscopy can reach one part in trillion levels. Therefore this method demonstrates the thermal effect that was generated on the specific tissue, and the energy-absorbing nanoparticles can be imaged inside the body using this method.

As one example, a solution or formulation containing the ferromagnetic-antibody labeled nanoparticles is administered by injection to a human or animal patient human patient. The antibody, upon binding to its cellular target, forms a ferromagnetic-antibody labeled nanoparticle-cell complex. After a period of time, such as at least 2 hours up to 48 hours or more to allow clearance of the unbound ferromagnetic particles from the patient, the patient is placed in a magnetic field, such as that provided by an magnetic resonance imaging instrument or any other applicable instrument known to one skilled in the art. In various embodiments, the magnetic field is applied to a portion of the body, e.g., locally at the target site, or to the whole body.

The applied magnetic field heats the nanoparticles. The degree of heat production in the particles induces an expansion of the nanoparticles that is recorded by an ultrasonic transducer previously described. The patient is maintained in the magnetic field until a diagnostic or therapeutic temperature of 42° C. to 56° C. is reached. The heat production is controlled to achieve this temperature and hence to treat only tumor cells. The acoustic sound produced from the nanoparticle at the site is evaluated and correlated with the presence or absence of malignant cells at the target site by photoacoustic imaging and/or ultrasound spectroscopy.

In embodiments, the described photoacoustic imaging may be combined with other imaging techniques such as X-ray, MRI, CT, and PET scans. In instances where the tumor is light accessible, optical coherence tomography (OCT) combined with photoacoustic imaging may be used.

In various embodiments, the method comprises providing a described nanoparticle composition, e.g., a nanoparticle labeled with an antibody, and providing an energy source which causes the nanoparticle to increase in temperature, resulting in heating tissue and cells in the tissue of an animal, particularly a human patient, at least to the temperature sufficient to kill or damage the cells, in conjunction with photoacoustic imaging and/or ultrasound spectroscopy, where a desired temperature is achieved using an energy source and an imaging technique. As described, an energy source, such as a magnetic energy source, can be used which substantially penetrates the tissue, and thus allows activation of nanoparticle compositions, e.g., ferromagnetic nanoparticles, which may be located within deep tissue sites, or an energy source, such as light, may be used for surface or sub-surface activation of a nanoparticle composition. For example, in cases of surface tumors or tumors accessible by catheter, a carbon nanoparticle composition may be used which is activated or heated using light or electromagnetic radiation.

In one embodiment, any of the described methods for hyperthermally treating cells, including the use of magnetic or gold nanoparticles, may be combined with platelet-derived therapy. In one embodiment, platelet-derived therapy comprises obtaining platelets from the patient's blood, coating the platelets with antibodies, and reintroducing the coated platelets into the patient. In one embodiment, the antibodies are anti-tumor antibodies. In one embodiment, the coated platelets are reintroduced by injection into the patient's circulatory system after an initial hyperthermia therapy. The coated platelets travel though the blood vessels reaching the tumor surface where, due to the prior hyperthermia-induced tumor cell damage, the injected coated platelets attach to the tumor and its associated vascular supply, creating a blood clot or thrombus, which obstructs the blood supply to the tumor, and nutritionally starves the tumor. In one embodiment, additional or subsequent hyperthermia therapy treatments may be conducted during or following the platelet-derived therapy. In one embodiment, the platelets are coated with an antibody. This may be accomplished by methods as disclosed in, e.g., Iyer et al. (Meth. Mol. Biol. 2011; 751:553-563, Single-step conjugation of antibodies to quantum dots for labeling cell surface receptors in mammalian cells, which is incorporated by reference in its entirety herein. Using such methods, cell surface receptors in platelets are labeled using antibody-conjugated semiconductor quantum dots. In one embodiment, the quantum dots are ferromagnetic, and as described above, upon exposure to a magnetic energy source, provide hyperthermia therapy. The hyperthermia therapy provided by the platelet-coated antibody-quantum dot conjugate can be in addition to the hyperthermia therapy provided by the nanoparticle, or it can be the sole source for the hyperthermia therapy. In one embodiment, any of the described methods and compositions, such as hyperthermia treatment with photoacoustic imaging, may be used for treating diseases or infections due to bacterial, fungal, viral, and/or protozoan organisms. In one embodiment, a described method may be systemically applied, e.g., intravenous administration of the described composition. In one embodiment, the nanoparticle is labeled with an antibody which recognizes the infectious agent. In one embodiment, the nanoparticle is a ferromagnetic nanoparticle. In one embodiment, any of the described nanoparticles are conjugated with an antibody that binds to, or associates with, an infectious agent, e.g., an anti-bacterial antibody, anti-viral antibody, anti-fungal antibody, anti-parasitic antibody, and the like. In this embodiment, the conjugated nanoparticle composition is locally or systemically administered and subjected to radiation, such as electromagnetic radiation or alternating magnetic field, to achieve temperatures of between about 40° C. to about 49° C. in one embodiment, or between about 42° C. to about 49° C., or higher as needed to destroy the micro-organism(s). The toxins from the infectious agent can be removed from the blood through a dialysis system. In one embodiment, the method may be combined with additional therapies, including antibiotics, anti-fungal agents, anti-viral agents, etc. In various embodiments, following the method, the patient's blood is processed through an extracorporeal dialysis system, which removes or reduces the infectious agent, e.g., bacteria, and their associated toxins from the blood. In one embodiment, the dialysis system further comprises a magnetic separator, which allows separation and collection of nanoparticles, e.g., ferromagnetic nanoparticles, along with damaged infectious agent, e.g., bacteria, from the blood. In embodiments where a tumor is subjected to the described hyperthermia treatment, the circulating tumor cells can be collected by the magnetic separator along with the nanoparticles in the dialysis machine. In another embodiment, the patient's blood is exposed extracorporally to a localized alternating magnetic field prior to the blood being processed by a dialysis machine, such that the infectious agent, their associated toxins, and/or damaged tumor cells are separated and removed before recirculating the blood into the patient again, which prevents release of toxins inside the patient's body.

In one embodiment, any of the described methods and compositions, such as hyperthermal treatment with photoacoustic imaging, are used to ameliorate a neurodegenerative disease, e.g., Alzheimer's disease, Parkinson's disease, and the like. In one embodiment, the described nanoparticle, such as colloidal gold or ferromagnetic, is conjugated with an antibody that binds to, or associates with, beta amyloid peptide which forms plaques found in the brain of Alzheimer's patients. In one embodiment, the neurodegenerative disease-targeted nanoparticle is injected into the cerebrospinal fluid. The neurodegenerative disease-targeted nanoparticle may be subjected to electromagnetic radiation, such as microwave or RF, or alternating magnetic field, to achieve temperatures ranging between about 45° C. to about 55° C., for a period sufficient to reduce or prevent aggregation of beta amyloid peptides and/or to destroy beta amyloid peptide aggregates.

In one embodiment, the nanoparticle is colloidal gold. In various embodiments, the shape of the colloidal gold nanoparticle may be spherical, rod-shaped, irregular, etc. In one embodiment, the gold nanoparticle is rod-shaped, e.g., a nanorod, and may be subjected to surface plasmon resonance (SPR), which may be used as an imaging technique and/or as a means for heat generation for hyperthermia treatment, depending on the wavelength of the electromagnetic energy, e.g., near infrared light, and the axial diameter of the nanorod.

In one embodiment, the nanoparticle used in any of the described methods has (poly)ethylene glycol (PEG) groups attached. Methods to conjugate with PEG are known in the art and include, but are not limited to, encapsulating the nanoparticle and/or associating PEG with the nanoparticle. In embodiments, a targeting group is associated with the conjugated PEG; examples of such targeting groups include but are not limited to an antibody or a portion thereof, a ligand for a receptor, or other moieties that promotes association, retention, targeting, transport, and/or uptake of the described nanoparticle.

In one embodiment, the described nanoparticle, e.g., a pegylated colloidal gold or ferromagnetic nanoparticle, is configured as a drug carrier. In this embodiment, the nanoparticle is associated with a drug and facilitates or effects drug delivery by, e.g., drug administration, dispersion, targeting, controlled delivery (e.g., time-release), and the like. For example, hydrophobic drugs often require encapsulation or other means in order to increase the drug water solubility. In one embodiment, a drug is associated with a nanoparticle, such that the association may be covalent or non-covalent; in the case of a covalent association, the drug may be tethered to the nanoparticle by a linking moiety. In one embodiment, a drug-associated nanoparticle is used in one of the described methods, such as hyperthermal treatment, in combination with a role as a drug delivery vector, such that, e.g., a target site (e.g., tumor) may be subjected to both hyperthermal treatment and drug treatment, In one embodiment, a thermoacoustic imaging technology is used with the tumor cells and tumor stem cells. Known photoacoustic technology uses light-induced heat, producing expansion, to create an ultrasonic sound that is recorded by an ultrasonic transducer. The site is imaged as previously described. Photoacoustic technology is, however, limited by the penetration of the electromagnetic wavelengths from ultraviolet (UV) to far infrared (IR). The maximum penetration depth depends on the wavelength of the light that penetrates the tissue, e.g., 1-2 cm. Even with photoacoustic tomography (PAT), the maximum depth that can be imaged in the tissue is about 7-8 cm.

With the use of thermoacoustic imaging using heat sensitive antibody-coated nanoparticles and heating the coated-nanoparticle complex (e.g., microwaves, radiofrequency waves, focused ultrasound, etc.) one can image the thermal expansion of intended tissue, e.g., tumor, etc. regardless of the tumor depth in the body. The same concept applied for creating an image using "photoacoustic"/thermoacoustic imaging, using magnetic antibody-coated nanoparticles with a reversible magnetic field. In both of these embodiments, MRI thermal imaging is also able to image the thermally treated tissue. Similarly one can heat the desired tissue with a focused ultrasound with one transducer, and observe the temperature rise through the photoacoustic technology.

As described above, in various embodiments, a combination of hyperthermal treatment and imaging is provided. In one embodiment, the nanoparticle is colloidal gold which allows for hyperthermal treatment, as described above, as well as imaging using SERS. In various embodiments, the colloidal gold nanoparticle is associated with quantum dots and/or Raman reporters. In one embodiment, the colloidal gold nanoparticle, associated with quantum dots and/or Raman reporters, is also associated with or encapsulated by PEG. Further, as described above, the PEG may be further associated with a targeting moiety, such as an antibody or a portion thereof.

Thermotherapy Using a Magnetic Conformer

Magnets are found in nature and can be formed into any shape. All magnets have the characteristics of absorbing other magnetic elements, e.g., iron. Electromagnets are produced by wrapping a wire as a coil around iron of any shape, size, or conformation. In an electromagnet the magnetic pole depends on the direction of the electrical flow in the surrounding wire and remains stable as long as electricity flows in the same direction. If the electrical flow is turned off, the electromagnet loses its magnetism. If the direction of the current is changed, the magnet changes its polarity and becomes an alternating magnet.

In one embodiment, the method uses a magnetic conformer. This conformer can be a natural magent or an electromagnet in which the magnetic field is not reversed. In such an embodiment, the treatment modality is applied either locally, systemically, or both locally and systemically depending on the lesion and malignancy. When the treatment modality is applied systemically, the tumor has potentially metastasized in the body and the entire body is in need of thermotherapy. The localized magnet with stable magnetic field collects the circulating ferromagnetic nanoparticles or nanowires in the tissue near its magnetic field. Nanowires, so-named because the width is smaller than the length, can be metallic (e.g., Ni, Au), semiconductor (Si, InP, GaN, etc.), organic, or inorganic and have greater efficiency converting light to energy.

In one embodiment, the localized magnet with a stable magnetic field attracts the ferromagnetic radioactive and/or drug coated nanoparticles or nanowires in tissue or in a benign or malignant tumor near its magnetic field. As in the general method disclosed herein, the nanoparticles or nanowires may be coated with anti-tumor antibody, contain therapeutic agent(s) (e.g., genetic agent (DNA, RNA), radioactive agent, chemical agent (chemotherapeutic, antimicrobial, etc.)) in any combination.

Figure 6:
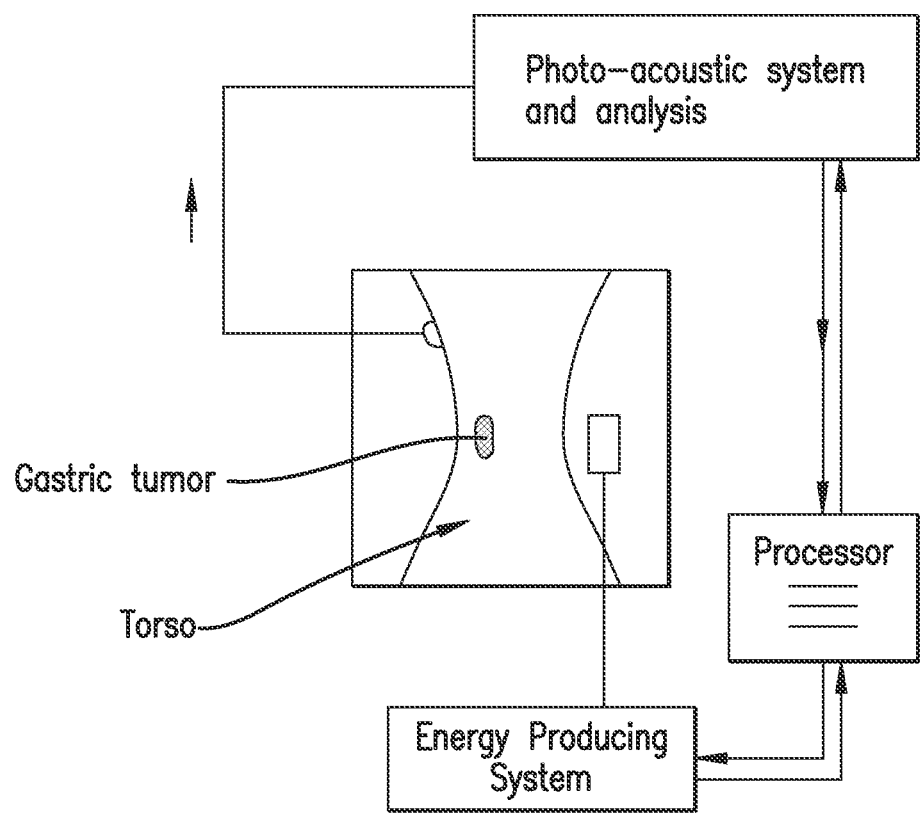
FIG. 6 shows the relationship between the photoacoustic system, the processor, and the energy delivery system.

In one embodiment, the photoacoustic or thermoacoustic component of the thermotherapy system described herein is connected to a processor that is connected to the thermal energy producing system (FIG. 6). This embodiment permits specific control of the amount of energy delivered and maintained at the lesion site to create a specific temperature at the nanoparticle- or nanowire-cell complex site.

In one embodiment, the treatment modality is applied either locally or systemically but preferentially localized to a defined or partially defined tumor site with no systemic metastasis. The method is further disclosed using a choroidal melanoma of the eye, but as one skilled in the art will appreciate the method is not so limited and is applicable to practically any part and/or body system of the body (skin, mucosa, prostate, brain, vertebra, extremities, urogenital system, endocrine system, gastrointestinal system, pancreas, breast, etc.).

The general use of radioactive nanoparticles in a method for treatment of eye tumors has been fully disclosed previously. In the embodiment currently described, magnetic nanoparticles or nanowires and a conforming magnet, also termed a magnetic conformer, are used in conjunction with photoacoustically controlled temperature measurement. This is achieved by connecting the electromagnetic conformer, in this case as the source of energy delivery, to a processor that is in turn connected to the photoacoustic system, to adjust the desired temperature level at the lesion site and is to a predetermined level. As previously disclosed, energy sources can be electromagnetic radiation, microwave radiation, radiofrequency (RF) radiation, ultrasound radiation, an alternating magnet, etc.

In one embodiment using an electromagnet, a simple magnet is positioned externally at or near a tumor site, or internally at or near a tumor site by a minimally invasive surgical procedure to attract circulating ferromagnetic nanoparticles or nanowires. The magnet size depends on the tumor or lesion size. For positioning in the eye, the magnet will be relatively small in comparison for positioning in or near breast, bone, or soft tissues. The magnet shape, like magnet size, is variable and flat, concave, semicircular, circular, annular etc. shapes may be used depending on the tumor or lesion location.

The simple magnet is an electric coil that is positioned around a metal, with a positive pole and a negative pole. To produce an alternating magnet, an electrical switch is used to rapidly change the direction of electricity and change the magnetic pole of the metal with an alternating frequency of 1 per second to 1 per nanosecond and producing a magnetic field of, e.g., about $1 \times 10^{-6}$ Tesla to 10 Tesla. Prior to converting the magnet to an alternating magnet, the nanoparticles circulating in the blood or lymphatic fluid or provided at a specific site are concentrated in the area of the localized magnet with a stable magnetic field.

Using the electrical switch, the magnet is made to rapidly alternate its polarity, i.e., producing an alternating magnetic field. The nanoparticles or nanowires located in the alternating magnetic field of the coil develop a semicircular motion. The rapid polarization alternation creates heat in the nanoparticle or nanowire. Because the nanoparticles or nanowires are concentrated at or near the tumor site, the heat that is generated heats the nanoparticle-cell or nanowire-cell complex at or near the target site.

In one embodiment, the nanoparticles are injected into the circulatory system. While other administration methods are within the inventive scope, the ease and convenience of direct intravenous injection, or less routinely intraarterial, injection makes this route attractive and provides a rapid route to reach all organs. Topical, intrathecal, subcutaneous, submucosal, inhalation, oral, cerebrospinal fluid injection, or intracavity (bladder, uterus, etc.) administration routes are possible to directly reach tumors or lymph nodes.

Regardless of the route of administration e.g. intravenously, of the nanoparticles, once in the body they are attracted selectively more to a magnet that is positioned in the localized area. Using the eye as a non-limiting example only, the conforming magnet can be placed externally on, or provided on a small probe to, an accessible ocular lesion, or the conforming magnet may be implanted on an internal lesion, e.g., under the conjunctiva, over the sclera, etc.

After a period of time post administration of 1 min to 15 min, sufficient to concentrate the nanoparticles or nanowires at a target site, they are preferentially treated by the disclosed method of thermotherapy. The presence of the magnetic conformer converts the initially stable magnet to a reversible magnetic capable of generating localized heat in the nanoparticle-cell or nanowire-cell complex, without displacing their location. In alternative embodiments, or after removing the localized magnet, the lesion or whole body undergoes hyperthermal treatment generated by means other than a conforming magnet, e.g., electromagnetic radiation, microwave radiation, radiofrequency radiation, etc., with the controlled temperature using the photoacoustic processor system as previously described herein in detail.

In either embodiment, hyperthermal treatment involves generating heat from 37° C. degree to <60° C. in stepwise 1° C. to 3° C. increments gradually as desired for release of agents from the nanoparticle and damage to the tumor cells. The polymers carrying the agents release them during the heating process, i.e., when the temperature for the polymer stretching or melting occurs sufficient to release the agent. In embodiments where a combination of treatment modalities are applied, the combination of agent therapy and radiotherapy with thermal therapy provides synergistic treatment for the lesion or tumor.

The duration of therapy can vary from 0.5 minute to 1-2 hours, depending upon the duration and therapy needed, as well as patient parameters, as one skilled in the art will be able to determine. In tumors that have metastasized, thermal treatment may be applied to the whole body after localized therapy. Using again the illustrative and non-limiting example of use of the method to treat an ocular lesion, the conformer can be directly applied on the cornea or the conjunctiva when a lesion is externally located. To treat ocular lesions that are not externally located, e.g., tumors located in the back of the eye or close to the optic nerve, a conjunctival incision is used to provide the conforming magnet to the area. The incision size depends upon the lesion size, and the magnet can be precisely located on or near the lesion site using, e.g., ophthalmoscopy, ultrasound, MRI, CT scan, PET scan, etc., as known to one skilled in the art. Once the location is verified, the magnetic conformer is temporarily placed and stabilized, e.g., sutured in place, to the scleral surface over or in the vicinity of the lesion for a desired time sufficient to accumulate an adequate amount of nanoparticles or nanowires at that site. The treatment can be repeated at any time as desired, and gauged by use of one or several imaging methods described.

Exsosomes are univesicular or multivesicular structures originating from the plasma membrane of all cells, including cancer cells. Exosomes serve in cellular waste management, but can also function between adjacent cells in intracellular signaling, and as a conduit to transfer genetic material between cells. In some circumstances, exosomes can "infect" adjacent cells or travel in the circulation and facilitate a metastatic process. Booth et al., J. Cell Biol. 172 (2006) 923.

Exosomes are much smaller than the cells from which they originate, typically exosomes are between 30 nm-100 nm. Their membrane, similar to those of other cells, is composed of protein and lipid layers. Exosomes carry proteins and genetic components (e.g., RNA, DNA) and have the same surface receptors as the cells from which they originate.

Exosomes thus carry biomarkers of their cell of origin, either a normal cell or a cancer cell, and thus can serve as a marker for the existence of cancerous cells. However, exosomes also may be used to evaluate the prognosis of a pathology, e.g., malignant tumors, infectious organisms, viral infection diseases, etc. An increase of exosomes originating from cancerous cells in the vascular system can be an indicator that a cancer is more of an aggressive type. The presence of exosomes in the vasculature may facilitate metastasis. There is no known therapy to target such exosomes, either circulating or localized.

An embodiment of the invention is a method using hyperthermal therapy applied to target either circulating or localized exosomes. This embodiment of the method simultaneously recognizes, quantifies, and destroys or reduces the number of exosomes, using hyperthermal therapy. The method is useful for both diagnostic and therapeutic applications. Quantification of exosomes is used for diagnosis of, e.g., a malignancy, an infection, etc., and can be performed either in vitro and/or in vivo. Destruction or reduction of exosomes is accompanied by destruction or reduction of the cancer cells from which they are produced, and is used in therapeutic applications.

In cancer immune therapy, the patient's circulating tumor exosomes can be cultivated, using tissue culture methods known in the art, with a population of the patient's growing defensive cells: antigen-presenting cells (APC), dendritic cells, and/or macrophages in order to sensitize these defensive cells. Upon intravenous injection back into the patient, these now sensitized defensive cells activate the patient's own T cells to attack both the tumor cells and the circulating exosomes originating from the tumor cells. The disturbed microenvironment of the tumor after thermotherapy using labeled nanoparticles and/or quantum dots contribute to making the remaining tumor cells accessible to the sensitized T cells. In addition, RNA and DNA is released from the damaged exosomes in the serum and, in turn, is damaged by oxidative molecules such as hydroxyl radicals and other reactive oxygen species in the serum, important for treatment of viral and infectious diseases.

The nanoparticles and/or quantum dots may contain polymers such as (poly)ethylene glycol, i.e., they may be PEGylated, to increase their longevity and biocompatibility, as subsequently described. The nanoparticles and/or quantum dots may be associated with cell penetrating peptides to enhance their uptake in the tumor cells. As only one non-limiting example, the nanoparticles and/or quantum dots may be associated and/or coated with a thermosensitive polymer (e.g., chitosan, chitin, etc.) to deliver compounds that are anti-tumor or anti-cancer agents. Such compounds include, but are not limited to, antineoplastic agents. Such agents include drugs and/or biologics. In one embodiment, the nanoparticles and/or quantum dots can be conjugated with humanized antitumor monoclonal antibodies designed for the treatment of cancers and for the treatment of bacterial, viral, and parasitic infections.

The content of exosomes can influence the function of the cells in which they come into contact, or in which they are taken up. A plurality of organic, non-organic, or synthetic nanoparticles alone or, with a plurality of quantum dots, are associated with various compounds to enhance their biocompatibility. Such compounds are known in the art and include, but are not limited to, (poly)ethylene glycol (PEG) and various PEG moieties, organic molecules, proteins such as biotin, short peptides, naturally occurring amino acids such as arginine or phenylalanine, mono- or bilayers of phospholipids, or biotargeted molecules etc. Association includes coatings, covalent attachments, and other types of associations sufficient to enhance biocompatibility. For example, the nanoparticles may be PEGylated to increase their longevity. The nanoparticles can consist of both inorganic or organic materials, as previously described. The particles can be entirely or partially biodegradable. The particles may also be included in or coated on a bioabsorbable or non-bioabsorbable but biocompatible polymer.

The nanoparticles are also conjugated with antibodies against the cell membrane's multiple exosome receptors and tumor cell membrane receptors. The conjugated and biocompatible nanoparticles, termed labeled nanoparticles, are attached to and/or taken up by both exosomes and the malignant or normal cells.

The labeled nanoparticles or quantum dots can be magnetic, paramagnetic, or nonmagnetic; gold, quartz, silicon, graphene, zinc oxide, ceramic, plastic, Particles of crystalline silicon may be monocrystalline cells, poly or multicrystalline cells, or ribbon silicon having a multicrystalline structure. The particles may be a nanocrystal of synthetic silicon, gallium/arsenide, cadmium/selenium, copper/indium/gallium/selenide, zinc sulfide, indium/gallium/phosphide, gallium arsenide, indium/gallium nitride, and are synthesized controlling crystal conformations and sizes. In one embodiment, the nanoparticle may comprise a nanocrystal, such as cadmium/selenium (Cd/Se), and a metal. For example, a CdSe/Au nanometer-sized composite particle may be synthesized through a two-step procedure, where CdSe nanorods are formed by the reaction of Cd and Se precursors in a mixture of trioctylphosphine oxide and an alkylphosphonic acid to form rod-shaped CdSe nanoparticles, and the CdSe rods are treated with a mixture of gold chloride, didodecyldimethylammonium bromide, and hexadecylamine to stabilize the nanocrystals and to reduce the gold chloride to elemental gold. Because the two ends of the CdSe rods differ crystallographically, and therefore chemically, control of growth conditions allows growth of Au particles preferentially on one end of each rod. In addition to CdSe/Au particles, one skilled in the art will readily recognize that particles can be constructed from a variety of other semiconductor/metal and semiconductor/semiconductor hetero-junctions. For example, particles based upon semiconductor/metal heterojunctions between group II-VI, IV, III-V, IV-VI, referring to groups of the periodic table, metal-oxide, or organic semiconductors and a metal, and in particular those based upon Si/Au, GaAs/Au, InAs/Au, and PbS/Au hetero-junctions, can be used in the same way as those discussed here and one or more combinations of these can be used.

The size of the nanoparticles is between 1 nm-100 nm. In one preferable embodiment, the size of the nanoparticles is between 1 nm-10 nm. In this embodiment, the nanoparticle size is about an order of magnitude smaller that the exosome size.

Exosomes circulate in body fluids and, because of their small size, they cross the blood brain or blood ocular barrier and are taken up by normal cells or tumor cells. The labeled nanoparticles attach to the exosomes.

The labeled nanoparticles or quantum dots, when injected into the body, seek the exosomes and cell membrane receptors on cells such as tumor cells. As a result, the nanoparticle or quantum dot-conjugated exosomes are present in the circulation. The nanoparticles and/or quantum dots are excreted completely in the urine. As a result, the nanoparticle and/or quantum dot-conjugated exosomes can be detected extra corporally in a body fluid sample, e.g., blood, extra and intraocular fluid, cerebrospinal fluid, sputum, nasal secretions, urine, sweat, etc.

The complex of exosomes and nanoparticles and/or quantum dots can be detected and quantitated using various methods.

One quantitation and detection method uses that disclosed in U.S. Pat. No. 8,119,165 for detecting circulating malignant cells. The complex of nanoparticles and/or quantum dots-exosomes are heated using external thermal energy, e.g., electromagnetic, ultraviolet, visible, infrared, microwave, radiofrequency radiation, ultrasound, reversible magnetic field, etc. or a combination of these. The increased temperature in these complexes is measured using photoacoustic technology as described in U.S. Pat. Nos. 8,121,663 and 8,554,296. The thermal energy is preferentially absorbed by the nanoparticles and/or quantum dots, thus the temperature of the nanoparticles and/or quantum dots rises much more rapidly than the temperature of the tissues or cells to which they are attached or taken up. The temperature rise causes physical expansion of the nanoparticles and/or quantum dots, producing a sound wave that can be measured, imaged, and counted by a photoacoustic system. The temperature variation can also be measured precisely with this technique, demonstrating either an increase or decrease of the sound wave amplitude in photoacoustic imaging or tomography. The acoustic signal is measured and related to the temperature of the nanoparticle complex to effect hyperthermal therapy. The method can be combined with flow cytometry for cell quantitation. The quantitation and detection method can be used ex vivo, e.g., on body fluid samples.

Another ex vivo quantitation and detection method is by application of various wavelengths of light to the samples. The complex produces a visible response based on light exposure, e.g., fluorescence, and the visible response can be quantified by a detector and processed by a computer.

Other ex vivo quantitation and detection methods include standard methods that include flow cytometry, microscopy, mass spectroscopy, bioformatic analysis, etc.

In one embodiment, the nanoparticle and/or quantum dot complex may contain or be associated with various therapeutic compounds using a thermosensitive coating, e.g., a thermosensitive polymer as known in the art. Therapeutic compounds include, but are not limited to, anti-infective agents, anti-viral agents, anti-parasitic agents, anti-fungal agents, antiproliferative agents, enzyme inhibitors or modulators, anti-VEGF, gene suppressants, gene stimulators, etc., as known in the art. In this embodiment, increasing the temperature of the complex by hyperthermal therapy of nanoparticles and/or quantum dots and exosomes to about 39° C.-41° C. releases the compound from the thermo sensitive polymers associated with the nanoparticle/quantum dot carriers. Further temperature increases to 43° C.-45° C. or 47° C.-50° C. or higher adversely affect the exosome membrane, rendering the exosome more vulnerable to the therapeutic agents released from the nanoparticles or administered at lower dose orally or systemically. This controlled thermotherapy can be combined with other standard therapies for cancer, e.g., radiation, immune, or vaccine therapy etc. Simultaneously a second plurality of nanoparticles and/or quantum dots may be administered containing other agents, e.g., small molecules, other therapeutics including but not limited to gene therapy, to fight the disease process.

The temperature increase is related to the amount of energy applied. The photoacoustic system measures the temperature of the nanoparticle and/or quantum dot, and communicates by a processor with the energy delivery system to control the amount of energy delivery to the complex of nanoparticles and/or quantum dots and exosomes at a predetermined level.

In one embodiment, the nanoparticles and/or quantum dots provides therapeutic agents in addition to its hyperthermal effect. In this embodiment, the nanoparticles and/or quantum dots may provide immune-stimulatory agents, vaccines, and other therapeutic compounds known in the art. As only one non-limiting example, the nanoparticles and/or quantum dots may be associated and/or coated with a thermosensitive polymer (e.g., chitosan, chitin, etc.) to deliver compounds that are anti-tumor or anti-cancer agents. Such compounds include, but are not limited to, antineoplastic agents. Such agents include drugs and/or biologics. Antineoplastic drugs include cisplatin, carboplatin, tetraplatin, iproplatin, adriamycin, mitomycin C, actinomycin, ansamitocin and its derivatives, bleomycin, Ara-C, daunomycin, metabolic antagonists such as 5-FU, methotrexate, isobutyl 5-fluoro-6-E-furfurylidene-amino-xy-1,2,3,4,5,6 hexahydro-2,4-dioxopyrimidine-5-carboxylate, melpharan, mitoxantrone, lymphokines, aclacinomycins, chromycins, olivomycins, etc. Antineoplastic biologics include DNA, RNA, protein, siRNA, genes or portions thereof, etc.

In this embodiment the immune response is stimulated, e.g., to facilitate removal of the hyperthermally-damaged tumor cells and their circulating exosomes, to target infectious agents, etc.

Exosomes play a role in Alzheimer's disease by facilitating aggregation and accumulation of beta-amyloids proteins. Therapies that facilitate their removal would facilitate treatment. Stimulated microglial cells may be activated by adding therapeutic agents to the complex of nanoparticles and/or quantum dots and exosomes. The complex may be administered orally, systemically, or injected into a body cavity. The use of combined nanoparticles and/or quantum dots and exosomes enhances cellular uptake of genes that can provide combined genetic therapy with more conventional drug therapy, enhancing attach of a disease process.

In one embodiment, neurodegenerative diseases such as Alzheimer's disease or Parkinson's disease may be treated by the inventive method using nanoparticles and/or quantum dots containing antibodies against beta-amyloid protein, e.g. Crenezumab, etc. These nanoparticles and/or quantum dots, which may be 1 nm-5 nm, pass through the blood brain barrier and penetrate into areas not previously accessible to such treatment. This embodiment of the method can be used for treatment of degenerative disease of the central nervous system and/or the eye.

EXAMPLE

Figure 2:
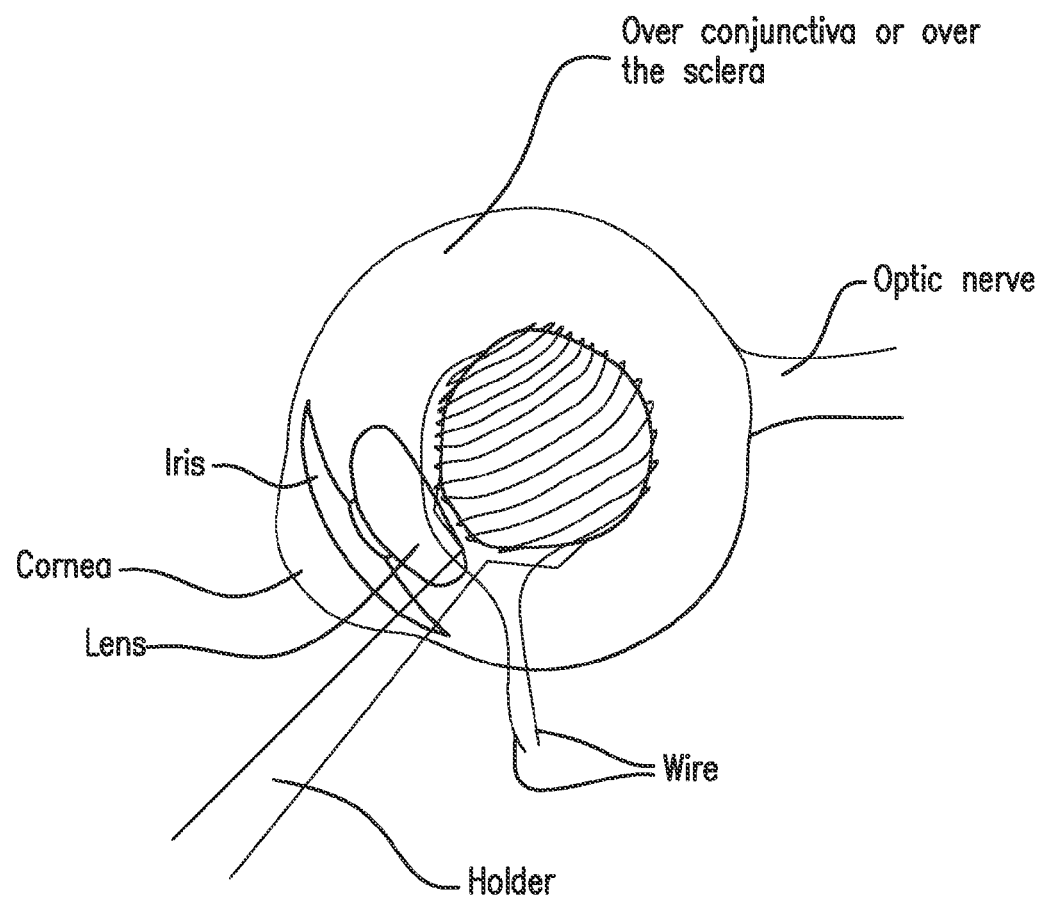
FIG. 2 illustrates therapy of a patient with a choroidal tumor.
Figure 3:
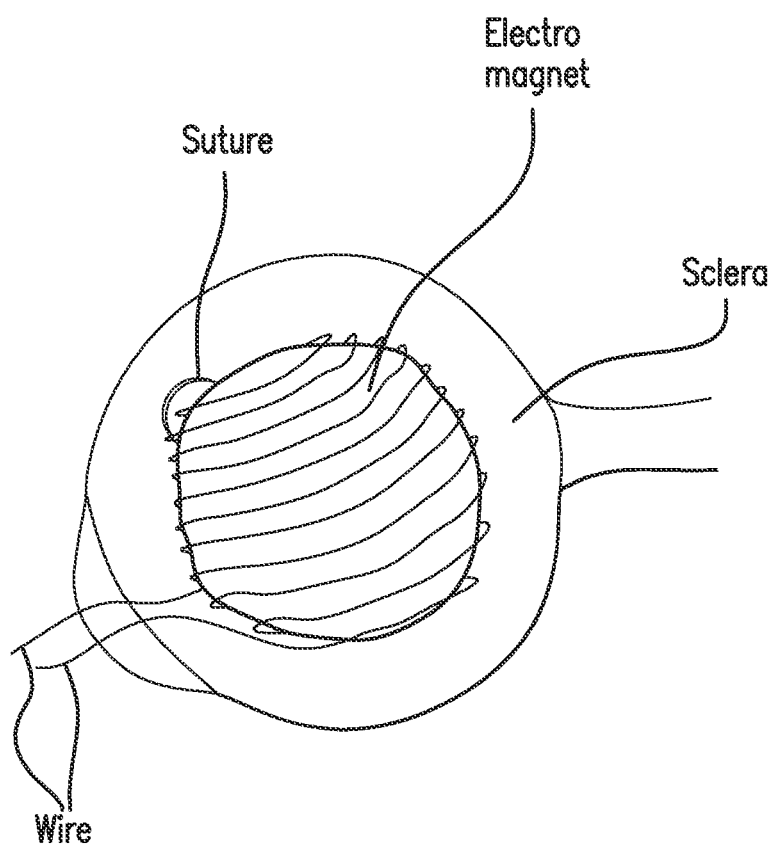
FIG. 3 illustrates electromagnet administration non-invasively, through the conjunctiva to the tumor.

FIG. 2 illustrates a patient with a choroidal tumor, diagnosed clinically as malignant melanoma. The patient is treated with the inventive thermotherapy using ferromagnetic nanoparticles coated with (poly)ethylene glycol, anti-tumor antibody, and a polymer having anti-cancer medication that releases the medication when the temperature reaches 42° C. The ferromagnetic nanoparticles are also coated with radioactive molecules that emit α or β radiation with a short half-life (e.g., 3 hours to days). The nanoparticles are administered intravenously to the patient. A natural magnet or an electromagnet is sutured to the sclera if the tumor cannot be covered with the magnet if placed externally as shown in FIG. 2. If the tumor is located anteriorly, an electromagnet is preferably applied non-invasively, through the conjunctiva to the tumor as shown in FIG. 3. After a waiting period, e.g., one minute to one hour, sufficient additional ferromagnetic particles are accumulated in the tumor. After the magnet is removed, the patient is treated locally by the same electromagnet using a rapidly alternating magnetic field. However, when it is desirable to treat the tumor and possible metastatic lesions, a large reversible magnet covering the entire body is used and the patient's entire body receives thermotherapy.

By rapidly reversing the magnetic field, the ferromagnetic nanoparticles are heated due to an internal semicircular motion in the individual ferromagnetic nanoparticles. The degree of heating is recorded by the photoacoustic system which, in turn, is communicated by a processor with the reversible magnet to generate the desired temperature at the tumor site. When the desired temperature is achieved, this desired temperature is maintained for a desired period, e.g., about 15 minutes in one embodiment, greater than 15 minutes in another embodiment. In general, the initial thermal energy is delivered to achieve a temperature of 42° C. to 43° C. to release the drugs from the nanoparticles. If needed, the temperature is gradually increased to, e.g., 45° C., 47° C., 50° C., or greater than 50° C. for a period, as needed. Parameters such as these are programmed by processor software that controls thermal energy delivery. FIG. 6 illustrates how information obtained from the photoacoustic system controls the energy delivery by the processor to achieve and maintain the desired temperature, for a desired time, in the nanoparticle-cell complex at the tumor or lesion site.

After thermotherapy is completed, the patient is administered topical antibiotics for a few days and remain under physician observation. The treatment may be repeated at intervals of 3 months to 9 months, or more or less frequently as needed, to destroy the tumor. The release of thermal energy, radioactivity, and drugs during the therapy generally gradually damages tumor cells and permits gradual patient recovery. Because the therapy is generally not invasive, or is only minimally invasive in embodiments where an internal magnet is used, the patient does not require long-term hospitalization. In a patient with severe disease, the patient may be treated with a low dose of anti-cancer medication to further kill the already damaged tumor cells, without damaging healthy cells.

Figure 4A:
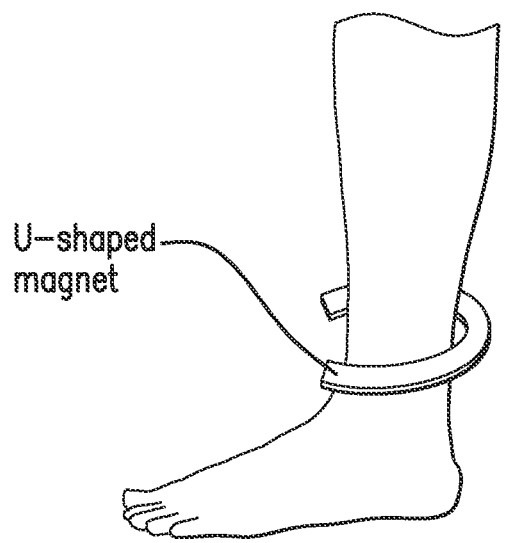
FIGS. 4A and 4B illustrate one embodiment after placement of the magnet for a tumor affecting the lower leg and with a horseshoe-shaped electromagnet configuration.
Figure 4B:
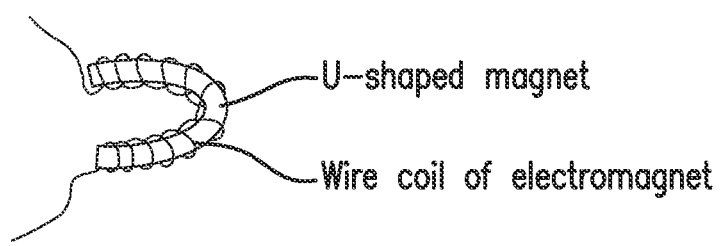

In one embodiment after placement of the magnet, the ferromagnetic nanoparticles, which may additionally be radioactive and/or contain a therapeutic agent, are concentrated at a benign or malignant tumor after systemic or local administration at a localized site, e.g., in the eye, skin, breast, extremities, CNS, spinal cord, vertebra, pelvis, urogenital system, tongue, throat, etc. Examples are shown in FIGS. 4A, 4B for a tumor affecting the lower leg and with a horseshoe-shaped electromagnet configuration, and in FIG. 5 for a facial skin tumor.

In one embodiment, the treatment of the tumor requires medication only. In this embodiment, the ferromagnetic nanoparticles carry medication in the absence of a radioactive molecule. The ferromagnetic nanoparticles may carry, e.g., immune modulators, anti-VEGF, sRNA, RNA, genes, bacteriophages, antibiotics, growth hormones, growth inhibitors, and combinations of these as desired.

The references disclosed and cited below are expressly incorporated by reference herein in their entirety.

Andor Technology, "Transport Across the Nuclear Membrane Using Quantum Dots," Aug. 23, 2011, available at www.andorcom/company/news/?docID=1224

Boyden, "Optogenetics: Using Light to Control the Brain," The Dana Foundation, Nov. 30, 2011, available at www-.dana.org/news/cerebrum/detail.aspx?id=34614

Buchen, "Illuminating the Brain," Nature, vol. 465, May 6, 2010, pp. 26-28.

Dixit et al., "Quantum Dot Encapsulation in Viral Capsids," Nano Letters, vol. 6, no. 9 (2006); pp. 1993-1999.

Deisseroth, "Optogenetics," Nature Methods, Published online Dec. 20, 2010. available at www.stanford.edu/qroup/dlab/papers/deisserothnature2010.pdf Deisseroth, "Optogenetics: Controlling the Brain with Light [Extended Version]," Scientific American, Published online Oct. 20, 2010, available at www.scientificamerican-.com/article.cfm?id=optogenetics-controllinq Dubertret et al., "In vivo Imaging of Quantum Dots Encapsulated in Phospholipid Micelles," Science, vol. 298, no. 5599 (2002), pp. 1759-1762.

Gill et al., "Fluorescence Resonance Energy Transfer in CdSe/ZnS-DNA Conjugates: Probing Hybridization and DNA Cleavage," J. Phys. Chem. B., vol. 109 (2005), pp. 23175-23179.

Joo et al., "Enhanced Real-Time Monitoring of Adeno-Associated Virus Trafficking by Virus-Quantum Dot Conjugates," ACSNano, vol. 5, issue 5 (2011); pp. 3523-3535.

Michalet et al., "Quantum Dots for Live Cells, in Vivo Imaging, and Diagnostics," Science, 307, no. 5709 (2005), pp. 538-544.

Yizhar et al., "Optogenetics in Neural Systems," Neuron, vol. 71 (2011), 9-34.

Zhang et al., "Optogenetic interrogation of neural circuits: technology for probing mammalian brain structures," Nature Protocols vol. 5, no. 3 (2010), pp. 439-456.

Olson et al., "In vivo characterization of activatable cell penetrating peptides for targeting protease activity in cancer," Integ. Biol., vol. 1, (2009) pp. 382-389.

Olson et al., "Activatable cell penetrating peptides linked to nanoparticles as dual probes for in vivo fluorescence and MR imaging of proteases," PNAS, vol. 107, no. 9, pp. 4311-4316 (2010), www.pnas.org/10.1073/pnas.0910283107

Jarnagin et al., "Treatment of cholangiocarcinoma with oncolytic herpes simplex virus combined with external beam radiation therapy," Cancer Gene Ther. 13 (2006) 326-34.

Nguyen et al. "Surgery with molecular fluorescent imaging using activatable cell-penetrating peptides decreases residual cancer and improves survival," PNAS, vol. 107, no. 9, pp. 4317-4322 (2010), www.pnas.org/10.1073/pnas.0910261107

Aguilera et. al., "Systemic in vivo distribution of activatable cell penetrating peptides is superior to cell penetrating peptides," Integ Biol (Camb), vol. 1., no. 5-6, pp. 371-381 (2009).

Alavarez-Lorenzo et al. "Temperature-sensitive chitosan-poly(N-isopropylacrylamide) interpenetrated networks with enhanced loading capacity and controlled release properties" J. Controlled Release 102(3), 629-641 (2005).

Alexander et al., Poly(N-Isopropylacrylamide)-Based Temperature-Sensitive Polymers. AAPS J. 2007; 9 (2) Nanotechnology and Drug Delivery, article 26 (www.aapsi.orq)

Benyettou et al. "Magnetoliposome for Alendronate Delivery" J. Mater. Chem., 21, 4818-4820 (2011).

Filipa et al. "Polyelectrolyte-coated Unilamellar Nanometer-sized Magnetic Liposomes" Langmuir 25(12), pp. 6793-6799 (2009).

Tai et al. "Thermosensitive liposomes entrapping iron oxide nanoparticles for controllable drug release" Nanotechnology vol 20, 135101 (2009).

Farokhzad et al. "Impact of Nanotechnology on Drug Delivery" ACS Nano 2009, 3(1), pp. 16-20.

Xu et al. "Controlled Release and Assembly of Drug Nanoparticles via pH-Responsive Polymeric Micelles: A Theoretical Study" J. Phys. Chem. B, 2012, 116 (20), pp 6003-6009.

Budgin et al. "Functionalization of Magnetic Nanoparticles with Amphiphilic Block Copolymers: Self-Assembled Thermoresponsive Submicrometer Particles" Langmuir, 2012, 28 (9), pp 4142-4151.

Balasubramaniam et al., "Poly(N-isopropylacrylamide)-Coated Superaramagnetic Iron Oxide Nanoparticles: Relaxometric and Fluorescence Behavior Correlate to Temperature-Dependent Aggregation" Chem. Mater., 2011, 23 (14), pp 3348-3356.

Pothayee et al. "Magnetic Block Ionomer Complexes for Potential Dual Imaging and Therapeutic Agents" Chemistry of Materials 2012 Article ASAP.

Pitt et al. "Triggered Drug Delivery Systems" Journal of Controlled Release Volume 2, November 1985, Pages 363-374.

Hoare et al., A Magnetically Triggered Composite Membrane for On-Demand Drug Delivery, Nano Lett., 2009, 9 (10), pp 3651-3657.

Mornet, Magnetic nanoparticle design for medical diagnosis and therapy, J. Mater. Chem., 2004,14, pp. 2161-2175.

Sexton et al. A Protective Vaccine Delivery System for In Vivo T Cell Stimulation Using Nanoengineered Polymer Hydrogel Capsules, ACS Nano, 2009, 3 (11), pp 3391-3400.

Although several embodiments have been chosen to illustrate the invention, those skilled in the art will readily appreciate that various changes and modifications can be made without departing from the scope of the invention.

What is claimed is:

1. A method providing diagnosis or therapy to a patient in need thereof, the method comprising administering to a patient a composition comprising a targeting agent- and/or antitumor-antibody-labeled nanoparticle and/or quantum dot, where the nanoparticle and/or quantum dot forms a targeting agent- and/or antibody-labeled nanoparticle and/or quantum dot-exosome complex, exposing the circulatory system of the patient to an energy source wherein the nanoparticle and/or quantum dot responds by expanding thus generating an acoustic signal, measuring the acoustic signal and relating the measured signal to a temperature of the nanoparticle and/or quantum dot exosome complex, and controlling the temperature of the nanoparticle and/or quantum dot exosome complex from about 39° C. to about 58° C. based on the acoustic signal to hyperthermally damage the exosome.

2. The method of claim 1 providing diagnosis of a pathology in the patient by quantitating the amount or concentration of the nanoparticle and/or quantum dot exosome complex, detecting a relatively increased amount or concentration of the nanoparticle and/or quantum dot exosome complex in the patient in need thereof compared to a control individual, and diagnosing the pathology based on the detected amount or concentration.

3. The method of claim 1 providing and assessing therapy to a pathology in the patient by quantitating the amount or concentration of the nanoparticle and/or quantum dot exosome complex, detecting a relatively decreased amount or concentration of the nanoparticle and/or quantum dot exosome complex in the patient in need thereof after thermal therapy compared to the patient in need thereof prior to thermal therapy, and assessing therapy based on the detected amount or concentration.

4. The method of claim 1 where the exosomes are the products of infectious cells or malignant cells.

5. The method of claim 1 where quantitating is by flow cytometry.

6. The method of claim 1 applying thermal therapy to a solid tissue using a targeting agent localizing the nanoparticle and/or quantum dot to the solid tissue.

7. The method of claim 1 applying thermal therapy to a fluid tissue using a targeting agent localizing the nanoparticle and/or quantum dot to the fluid tissue.

8. The method of claim 7 wherein the fluid tissue is blood and the exosomes are circulating in the vasculature.

9. The method of claim 1 optionally repeated a plurality of times on a patient having a relatively increased concentration of circulating exosomes originating from malignant cells, the method used to treat increased aggressiveness of the malignant cells.

10. The method of claim 1 further comprising infusing into the patient a population of the patient's exosomes that were subjected to in vitro co-culture with a population of the patient's defensive cells selected from the group consisting of antigen-presenting cells (APC), dendritic cells, macrophages, phagocytes, and combinations thereof.

11. The method of claim 1 where the nanoparticles and/or quantum dots are associated and/or coated with a thermosensitive polymer to deliver compounds that are anti-tumor or anti-cancer agents.

12. The method of claim 11 where the polymer is chitosan or chitin, and where the compounds are antineoplastic agents or anti-infectious agents.

13. The method of claim 1 where the nanoparticles and/or quantum dots are associated and/or coated with an agent to enhance biocompatibility.

14. A method providing diagnosis or therapy to a to a patient in need of neurodegenerative diagnosis or therapy, the method comprising administering to the patient a composition comprising an anti-beta-amyloid protein targeting agent-labeled nanoparticle and/or quantum dot of between 1 nm-5 nm in size, where the nanoparticle and/or quantum dot forms a targeting agent- and/or antibody: labeled nanoparticle and/or quantum dot exosome complex, exposing the circulatory system of the patient to an energy source wherein the nanoparticle and/or quantum dot responds by expanding thus generating an acoustic signal, measuring the acoustic signal and relating the measured signal to a temperature of the nanoparticle and/or quantum dot exosome complex, and controlling the temperature of the nanoparticle and/or quantum dot exosome complex from about 39° C. to about 58° C. based on the acoustic signal to hyperthermally damage the exosome and an associated beta-amyloid protein.

15. The method of claim 14 where the patent has a neurodegenerative disease of the eye, Alzheimer's disease, or Parkinson's disease.

16. The method of claim 14 where the anti-beta amyloid protein antibody is crenezumab.

* * * * *